United States Patent
Pratt et al.

(10) Patent No.: US 10,016,543 B2
(45) Date of Patent: Jul. 10, 2018

(54) DISPOSABLE REDUCED-PRESSURE THERAPY SYSTEM WITH ELECTRONIC FEEDBACK

(71) Applicant: KCI LICENSING, INC., San Antonio, TX (US)

(72) Inventors: Benjamin Andrew Pratt, Poole (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 972 days.

(21) Appl. No.: 14/472,738

(22) Filed: Aug. 29, 2014

(65) Prior Publication Data

US 2015/0094673 A1 Apr. 2, 2015

Related U.S. Application Data

(60) Provisional application No. 61/885,758, filed on Oct. 2, 2013.

(51) Int. Cl.
*A61M 1/00* (2006.01)
*A61M 39/22* (2006.01)
(Continued)

(52) U.S. Cl.
CPC ........ *A61M 1/0088* (2013.01); *A61M 1/0027* (2014.02); *A61M 1/0031* (2013.01);
(Continued)

(58) Field of Classification Search
CPC .............. A61M 1/0027; A61M 1/0088; A61M 1/0035; A61M 1/0031; A61M 2205/15;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 A1 3/1986
AU 745271 4/1999
(Continued)

OTHER PUBLICATIONS

Partial International Search Report for corresponding PCT/US2014/053452 dated Nov. 24, 2014.

(Continued)

*Primary Examiner* — Adam Marcetich

(57) ABSTRACT

Systems, methods, and apparatuses for providing feedback for reduced-pressure therapy are described. A regulator can include a supply chamber fluidly coupled to a dressing, a control chamber fluidly coupled to the dressing, a charging chamber fluidly coupled to the supply chamber through a port, and a regulator valve operable to control fluid communication through the port based on a pressure differential between the control chamber and a target pressure. The feedback system can include a printed circuit board, a pressure sensor and a signal interface communicatively coupled to the printed circuit board. The pressure sensor can be fluidly coupled to the control chamber to determine the pressure in the control chamber. The signal interface can indicate a state of the reduced-pressure therapy. A potential source can be communicatively coupled to the printed circuit board, the pressure sensor, and the indicator.

9 Claims, 7 Drawing Sheets

(51) Int. Cl.
F16K 31/385 (2006.01)
F16K 17/08 (2006.01)
G05D 16/06 (2006.01)

(52) U.S. Cl.
CPC ....... *A61M 1/0035* (2014.02); *A61M 2205/15* (2013.01); *A61M 2205/18* (2013.01); *A61M 2205/581* (2013.01); *A61M 2205/582* (2013.01); *A61M 2205/583* (2013.01); *F16K 17/085* (2013.01); *F16K 17/087* (2013.01); *F16K 31/3855* (2013.01); *G05D 16/06* (2013.01)

(58) Field of Classification Search
CPC ........ A61M 2205/18; A61M 2205/581; A61M 2205/582; A61M 2205/583; A61M 1/0025; A61M 2205/3344; F16K 31/3855; F16K 17/02; F16K 17/025; F16K 17/04; F16K 17/0406; F16K 17/085; F16K 17/087; Y10T 137/7836
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,140,726 A * | 7/1964 | Arenhold | G01F 1/34 137/510 |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,774,628 A * | 11/1973 | Norton | F16K 17/085 137/115.15 |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,246,788 A * | 1/1981 | Olin | G01N 1/2247 73/863.03 |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,532,814 A * | 8/1985 | Lalin | G05D 7/03 73/863.03 |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,705,065 A * | 11/1987 | McNeely | F16K 17/10 137/484.6 |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,782,849 A * | 11/1988 | Hodge | A61M 1/0037 137/103 |
| 4,787,888 A | 11/1988 | Fox | |
| 4,819,682 A * | 4/1989 | Van Marcke | F16K 31/404 137/1 |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,010,844 A * | 4/1991 | Takeuchi | A01J 5/048 119/14.25 |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,050,292 A * | 4/2000 | Richman | F16K 31/1266 137/495 |
| 6,071,267 A | 6/2000 | Zamierowski | |
| 6,135,116 A | 10/2000 | Vogel et al. | |
| 6,155,240 A * | 12/2000 | Amano | F02D 41/005 123/568.22 |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,553,306 B1 * | 6/2009 | Hunt | A61M 1/0031 604/304 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2002/0183702 A1 | 12/2002 | Henley et al. | |
| 2004/0118460 A1 * | 6/2004 | Stinson | A61M 1/0031 137/557 |

(56) References Cited

U.S. PATENT DOCUMENTS

| | | | |
|---|---|---|---|
| 2005/0167624 A1* | 8/2005 | Perez | F16K 31/3835 251/25 |
| 2006/0025727 A1 | 2/2006 | Boehringer et al. | |
| 2006/0079852 A1 | 4/2006 | Bubb et al. | |
| 2007/0219532 A1* | 9/2007 | Karpowicz | A61M 1/0031 604/540 |
| 2008/0271804 A1* | 11/2008 | Biggie | A61M 1/0088 138/137 |
| 2009/0157016 A1 | 6/2009 | Adahan | |
| 2010/0185048 A1* | 7/2010 | Lonky | A61M 1/0031 600/37 |
| 2010/0274229 A1* | 10/2010 | Duocastella Codina | A61M 1/0011 604/543 |
| 2011/0297252 A1* | 12/2011 | Hurley | G05D 16/163 137/488 |
| 2012/0109083 A1* | 5/2012 | Coulthard | A61F 13/02 604/319 |
| 2012/0123358 A1* | 5/2012 | Hall | A61M 1/0088 604/318 |
| 2012/0174995 A1* | 7/2012 | Bloomer | F16K 17/0453 137/535 |
| 2015/0094674 A1* | 4/2015 | Pratt | A61F 13/00068 604/318 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 3/1999 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2009086580 A1 | 7/2009 |
| WO | 2014043225 A2 | 3/2014 |

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., vol. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

(56) References Cited

OTHER PUBLICATIONS

G. Živadinovic, V. Đukić, Ž. Maksimović, Đ. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, "An Improved Sump Drain-Irrigation Device of Simple Construction," Archives of Surgery 105 (1972) pp. 511-513.

C.E. Tennant, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

\* cited by examiner

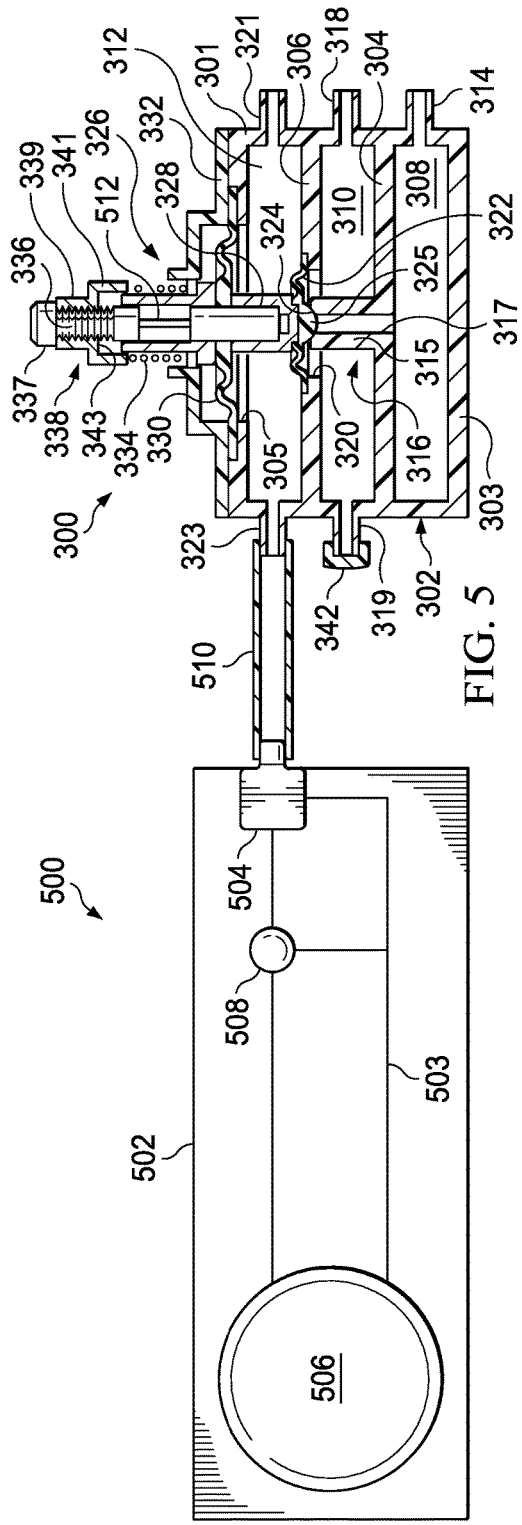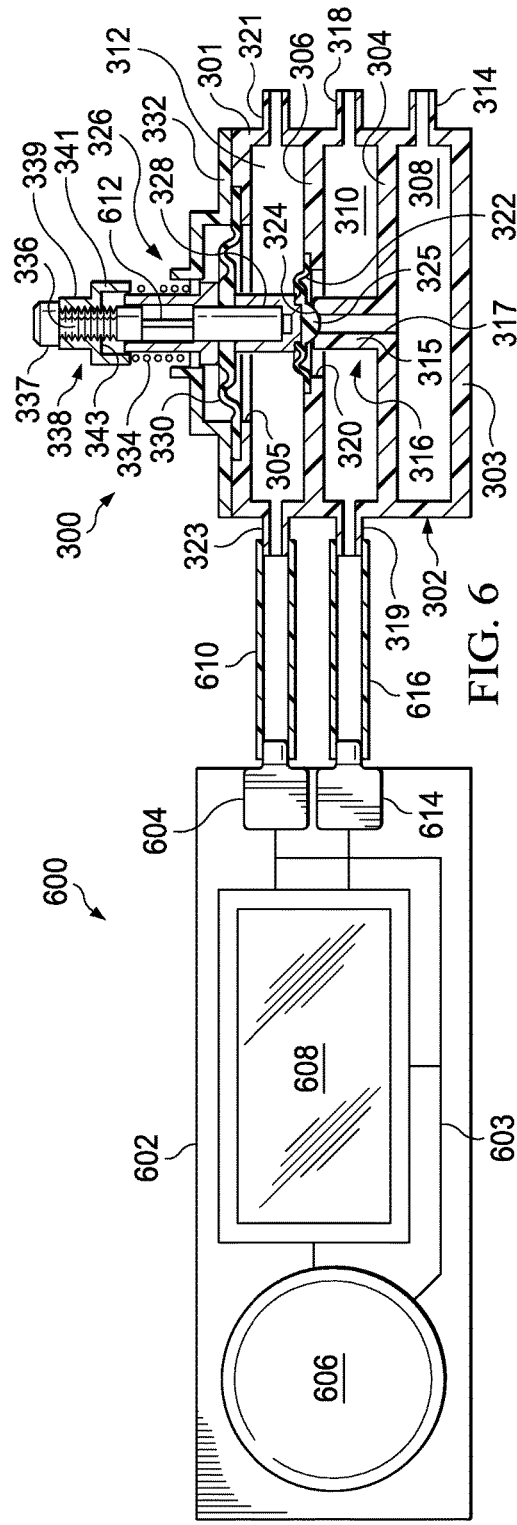

DISPOSABLE REDUCED-PRESSURE THERAPY SYSTEM WITH ELECTRONIC FEEDBACK

RELATED APPLICATION

The present invention claims the benefit, under 35 USC § 119(e), of the filing of U.S. Provisional Patent Application Ser. No. 61/885,758, entitled "DISPOSABLE REDUCED-PRESSURE THERAPY SYSTEM WITH ELECTRONIC FEEDBACK," filed Oct. 2, 2013, which is incorporated herein by reference for all purposes.

TECHNICAL FIELD

The subject matter described herein relates generally to monitoring reduced-pressure therapy and, more particularly, but not by way of limitation, to electronic feedback of reduced-pressure therapy supplied by a wall-suction source.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds with reduced pressure is commonly referred to as "reduced-pressure therapy," but may also be known by other names, including "negative pressure wound therapy" and "vacuum therapy," for example. Reduced-pressure therapy may provide a number of benefits, including migration of epithelial and subcutaneous tissues, improved blood flow, and microdeformation of tissue at a wound site. Together, these benefits can increase development of granulation tissue and reduce healing times.

While the clinical benefits of reduced-pressure therapy are widely known, the cost and complexity of reduced-pressure therapy can be a limiting factor in its application, and the development and operation of reduced-pressure systems, components, and processes continues to present significant challenges to manufacturers, healthcare providers, and patients.

SUMMARY

Illustrative embodiments of systems, methods, and apparatuses for regulating pressure are described below. One such illustrative embodiment may be described as a reduced-pressure system having a dressing, a regulator, and a feedback system. The regulator generally includes a supply chamber that can be fluidly coupled to the dressing through a supply lumen, a control chamber adapted to be fluidly coupled to the dressing through a feedback lumen, and a charging chamber fluidly coupled to the supply chamber through a port. A regulator valve can be coupled to the control chamber and operable to reciprocate at least partially within the control chamber to control fluid communication through the port based, at least in part, on a differential between a control pressure in the control chamber and a therapy pressure in the supply chamber. The feedback system may include a printed circuit board and a pressure sensor communicatively coupled to the printed circuit board. The pressure sensor can be fluidly coupled to the control chamber to determine the control pressure in the control chamber. The feedback system may also include an indicator, such as a signal interface, communicatively coupled to the printed circuit board and the pressure sensor. The indicator can be adapted to signal an operating state of the regulator. A potential source may also be communicatively coupled to the printed circuit board, the pressure sensor, and the indicator to provide electric potential to the printed circuit board, the pressure sensor, and the indicator.

Another illustrative embodiment relates to a method for regulating therapeutic pressure. The method generally includes fluidly coupling a manifold to a supply chamber through a supply lumen and fluidly coupling the manifold to a control chamber through a feedback lumen. The supply chamber can be fluidly coupled to a charging chamber, and the control chamber can be fluidly coupled to a pressure sensor. A charging pressure in the charging chamber can be reduced below a predetermined pressure, and fluid communication can be regulated between the supply chamber and the charging chamber based, at least in part, on a differential between a control pressure in the control chamber and a therapy pressure. The therapy pressure can be delivered from the supply chamber to the manifold, and a manifold pressure in the manifold can be fluidly communicated to the control chamber. The control pressure in the control chamber can be measured and a status of the control pressure in the control chamber can be indicated in response to measuring the control pressure in the control chamber.

Yet another illustrative embodiment relates to a feedback system for monitoring the application of reduced pressure therapy. The feedback system can include a printed circuit board and a pressure sensor. The pressure sensor can be communicatively coupled to the printed circuit board and adapted to be fluidly coupled to a control chamber to determine a control pressure. The feedback system may further include an indicator communicatively coupled to the printed circuit board and the pressure sensor, and may be configured to indicate a status of the control pressure. A potential source may also be communicatively coupled to the printed circuit board, the pressure sensor, and the indicator to provide electric potential to the printed circuit board, the pressure sensor, and the indicator.

Other features and advantages will become apparent with reference to the drawings and detailed description that follow.

BRIEF DESCRIPTION OF THE DRAWINGS

FIG. 5 is a schematic cross-section of an example embodiment of a feedback system using the regulator of FIG. 3A; and FIG. 6 is a schematic cross-section of an example embodiment of another feedback system using the regulator of FIG. 3A.

DETAILED DESCRIPTION

New and useful systems, methods, and apparatuses associated with monitoring pressure are set forth in the appended claims. Objectives, advantages, and a preferred mode of making and using the systems, methods, and apparatuses may be understood best by reference to the following detailed description in conjunction with the accompanying drawings. The description provides information that enables a person skilled in the art to make and use the claimed subject matter, but may omit certain details already well-known in the art. Moreover, descriptions of various alternatives using terms such as "or" do not necessarily require mutual exclusivity unless clearly required by the context. The claimed subject matter may also encompass alternative embodiments, variations, and equivalents not specifically described in detail. The following detailed description should therefore be taken as illustrative and not limiting.

The example embodiments may also be described herein in the context of reduced-pressure therapy applications, but many of the features and advantages are readily applicable to other environments and industries. Spatial relationships between various elements or to the spatial orientation of various elements may be described as depicted in the attached drawings. In general, such relationships or orientations assume a frame of reference consistent with or relative to a patient in a position to receive reduced-pressure therapy. However, as should be recognized by those skilled in the art, this frame of reference is merely a descriptive expedient rather than a strict prescription.

Figure 1:
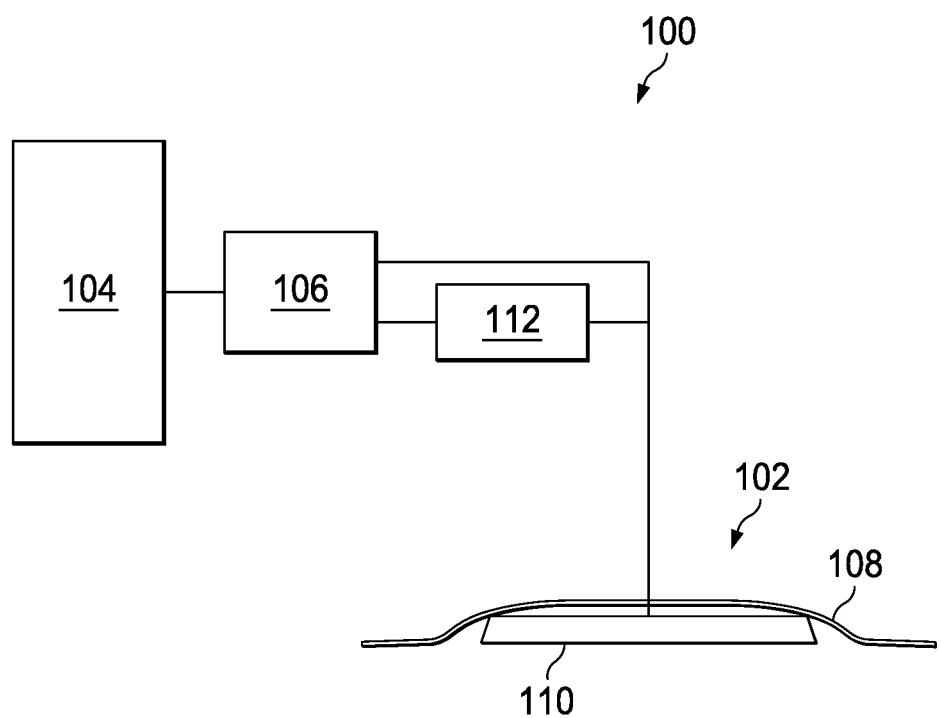
FIG. 1 is a functional block diagram of an example embodiment of a reduced-pressure therapy system that can regulate therapeutic pressure in accordance with this specification.

FIG. 1 is a simplified functional block diagram of an example embodiment of a reduced-pressure therapy system 100 that can regulate therapeutic pressure in accordance with this specification. As shown in the illustrative embodiment of FIG. 1, the reduced-pressure therapy system 100 may include a dressing 102 fluidly coupled to a reduced-pressure source 104. A regulator or controller, such as a regulator 106, may also be fluidly coupled to the dressing 102 and the reduced-pressure source 104. The dressing 102 generally includes a drape, such as a drape 108, and a tissue interface, such as a manifold 110. The reduced-pressure therapy system 100 may also include a fluid container, such as a container 112, fluidly coupled to the dressing 102 and the reduced-pressure source 104.

In general, components of the reduced-pressure therapy system 100 may be coupled directly or indirectly. For example, the reduced-pressure source 104 may be directly coupled to the regulator 106 and indirectly coupled to the dressing 102 through the regulator 106. Components may be fluidly coupled to each other to provide a path for transferring fluids (i.e., liquid and/or gas) between the components. In some embodiments, components may be fluidly coupled with a tube, for example. A "tube," as used herein, broadly refers to a tube, pipe, hose, conduit, or other structure with one or more lumina adapted to convey fluids between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

In operation, a tissue interface, such as the manifold 110, may be placed within, over, on, against, or otherwise adjacent to a tissue site. For example, the manifold 110 may be placed against a tissue site, and the drape 108 may be placed over the manifold 110 and sealed to tissue proximate to the tissue site. Tissue proximate to a tissue site is often undamaged epidermis peripheral to the tissue site. Thus, the dressing 102 can provide a sealed therapeutic environment proximate to the tissue site. The sealed therapeutic environment may be substantially isolated from the external environment, and the reduced-pressure source 104 can reduce the pressure in the sealed therapeutic environment. Reduced pressure applied uniformly through the tissue interface in the sealed therapeutic environment can induce macrostrain and microstrain in the tissue site, as well as remove exudates and other fluids from the tissue site. The removed exudates and other fluids can be collected in the container 112 and disposed of properly.

The fluid mechanics of using a reduced-pressure source to reduce pressure in another component or location, such as within a sealed therapeutic environment, can be mathematically complex. However, the basic principles of fluid mechanics applicable to reduced-pressure therapy are generally well-known to those skilled in the art, and the process of reducing pressure may be described illustratively herein as "delivering," "distributing," or "generating" reduced pressure, for example.

In general, exudates and other fluids flow toward lower pressure along a fluid path. This orientation is generally presumed for purposes of describing various features and components of reduced-pressure therapy systems herein. Thus, in the context of reduced-pressure therapy, the term "downstream" typically implies a position in a fluid path relatively closer to a reduced-pressure source, and conversely, the term "upstream" implies a position relatively further away from a reduced-pressure source. Similarly, it may be convenient to describe certain features in terms of fluid "inlet" or "outlet" in such a frame of reference. However, a fluid path may also be reversed in some applications, such as by substituting a positive-pressure source, and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of tissue that are not necessarily wounded or defective, but are instead areas in which it may be desired to add or promote the growth of additional tissue. For example, reduced pressure may be used in certain tissue areas to grow additional tissue that may be harvested and transplanted to another tissue location.

"Reduced pressure" generally refers to a pressure less than a local ambient pressure, such as the ambient pressure in a local environment external to a sealed therapeutic environment provided by the dressing 102. In many cases, the local ambient pressure may also be the atmospheric pressure in a patient's vicinity. Alternatively, the pressure may be less than a hydrostatic pressure associated with tissue at the tissue site. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

A reduced-pressure source, such as the reduced-pressure source 104, may be a reservoir of air at a reduced pressure, or may be a manual or electrically-powered device that can reduce the pressure in a sealed volume, such as a vacuum pump, a suction pump, a wall-suction port available at many healthcare facilities, or a micro-pump, for example. A reduced-pressure source may be housed within or used in conjunction with other components, such as sensors, processing units, alarm indicators, memory, databases, software, display devices, or operator interfaces that further facilitate reduced-pressure therapy. While the amount and nature of reduced pressure applied to a tissue site may vary according to therapeutic requirements, the pressure typically ranges between −5 mm Hg (−667 Pa) and −500 mm Hg (−66.7 kPa). Common therapeutic ranges are between −75 mm Hg (−9.9 kPa) and −300 mm Hg (−39.9 kPa).

A tissue interface, such as the manifold 110, can generally be adapted to contact a tissue site or other layers of a dressing, such as the dressing 102. A tissue interface may be partially or fully in contact with a tissue site. If a tissue site is a wound, for example, a tissue interface may partially or completely fill the wound, or may be placed over the wound. A tissue interface may take many forms, and may be many sizes, shapes, or thicknesses depending on a variety of factors, such as the type of treatment being implemented or the nature and size of a tissue site. For example, the size and shape of a tissue interface may be adapted to the contours of deep and irregular shaped tissue sites.

Generally, a manifold, such as the manifold 110, for example, is a substance or structure adapted to distribute or remove fluids from a tissue site. A manifold may include flow channels or pathways that can distribute fluids provided to and removed from a tissue site. In one illustrative embodiment, the flow channels or pathways may be interconnected to improve distribution of fluids provided to or removed from a tissue site. For example, a manifold may be an open-cell foam, porous tissue collection, and other porous material such as gauze or felted mat that generally includes structural elements arranged to form flow channels. Liquids, gels, and other foams may also include or be cured to include flow channels.

In one illustrative embodiment, the manifold 110 may be a porous foam pad having interconnected cells adapted to distribute reduced pressure across a tissue site. The foam material may be either hydrophobic or hydrophilic. In one non-limiting example, the manifold 110 may be reticulated polyurethane foam such as GranuFoam® dressing available from Kinetic Concepts, Inc. of San Antonio, Tex.

In some embodiments, such as embodiments in which the manifold 110 may be made from a hydrophilic material, the manifold 110 may also wick fluid away from a tissue site while continuing to distribute reduced pressure to the tissue site. The wicking properties of the manifold 110 may draw fluid away from a tissue site by capillary flow or other wicking mechanisms. An example of a hydrophilic foam is a polyvinyl alcohol, open-cell foam such as V.A.C. White-Foam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

A tissue interface may further promote granulation at a tissue site if pressure within a sealed therapeutic environment is reduced. For example, any or all of the surfaces of the manifold 110 may have an uneven, coarse, or jagged profile that can induce microstrains and stresses at a tissue site if reduced pressure is applied through the manifold 110.

In some example embodiments, a tissue interface may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface may further serve as a scaffold for new cell-growth, or a scaffold material may be used in conjunction with the tissue interface to promote cell-growth. In general, a scaffold material may be a biocompatible or biodegradable substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The drape 108 is an example of a sealing member. A sealing member may be constructed from a material that can provide a fluid seal between two environments or components, such as between a therapeutic environment and a local external environment. The sealing member may be, for example, an impermeable or semi-permeable, elastomeric film or barrier that can provide a seal adequate to maintain a reduced pressure at a tissue site for a given reduced-pressure source. For semi-permeable materials, the permeability generally should be low enough that a desired reduced pressure may be maintained. An attachment device may be used to attach a sealing member to an attachment surface, such as undamaged epidermis, a gasket, or another sealing member. The attachment device may take many forms. For example, an attachment device may be a medically-acceptable, pressure-sensitive adhesive that extends about a periphery, a portion, or an entire sealing member. Other example embodiments of an attachment device may include a double-sided tape, paste, hydrocolloid, hydrogel, silicone gel, organogel, or an acrylic adhesive.

A "container," such as the container 112 in FIG. 1, broadly includes a canister, pouch, bottle, vial, or other fluid collection apparatus. The container 112, for example, can be used to manage exudates and other fluids withdrawn from a tissue site. In many environments, a rigid container may be preferred or required for collecting, storing, and disposing of fluids. In other environments, fluids may be properly disposed of without rigid container storage, and a reusable container could reduce waste and costs associated with reduced-pressure therapy.

In general, reduced-pressure therapy can be beneficial for wounds of all severity, but the cost and complexity of reduced-pressure therapy systems often limit the application of reduced-pressure therapy to large, highly-exudating wounds present on patients undergoing acute or chronic care, as well as other severe wounds that are not readily susceptible to healing without application of reduced pressure. Many developing regions may not have access to dedicated, electrically-operated reduced-pressure sources for reduced-pressure therapy. Instead, these regions may rely on wall-suction sources for the supply of reduced pressure. These wall-suction sources may be seen as a practical, suitable, and lower cost alternative to a dedicated therapy unit with electronic controls.

Wall-suction sources are capable of providing continuous, or nearly continuous, supplies of reduced pressure. However, wall-suction sources may provide a broad range of reduced pressures and may require an operator to select an appropriate reduced pressure to be supplied. If the reduced pressure is set too low at the wall-suction source, removal of exudates and other wound fluids from the tissue site will not occur. If the reduced pressure is too high, the reduced-pressure therapy may cause internal bleeding and further damage to a tissue site. For at least these reasons, treatment of a tissue site with reduced pressure provided by a wall-suction source requires regulation of the amount of reduced pressure delivered to the tissue site.

The reduced-pressure therapy system 100 may overcome these shortcomings and others by providing feedback and mechanical regulation of therapeutic pressure. In some embodiments, for example, a regulator can regulate fluid communication between a supply chamber and a charging chamber, and a feedback system can provide feedback to alert operators of an operating state of reduced-pressure therapy during the provision of reduced-pressure therapy. For example, a feedback system may provide an operator with an operating state of one or more of the following: a control pressure, a supply pressure, a differential between the control pressure and the supply pressure, a leak condition, a blockage condition, a canister full condition, and an overpressure condition. In some embodiments, the reduced-pressure therapy system 100 may provide a highly configurable system that is low cost, disposable, single-patient use, or reusable.

Regulators

Figure 2A:
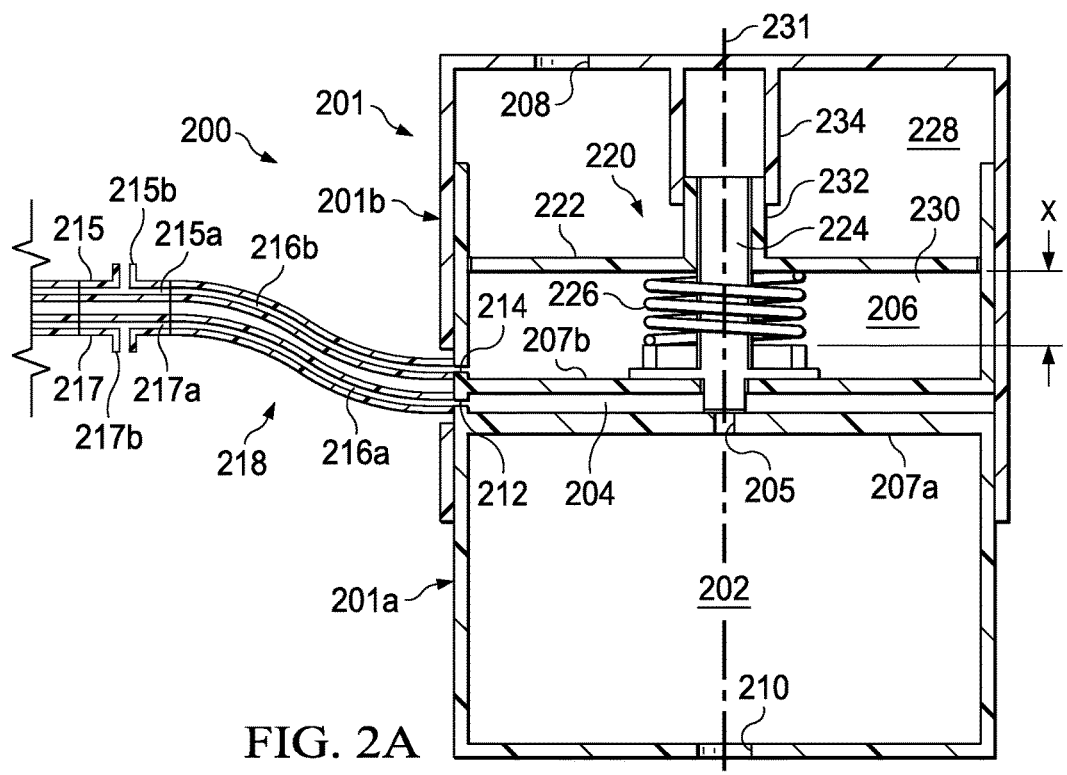
FIGS. 2A-2B are schematic cross-sections of an example embodiment of a regulator in the reduced-pressure therapy system.
Figure 2B:
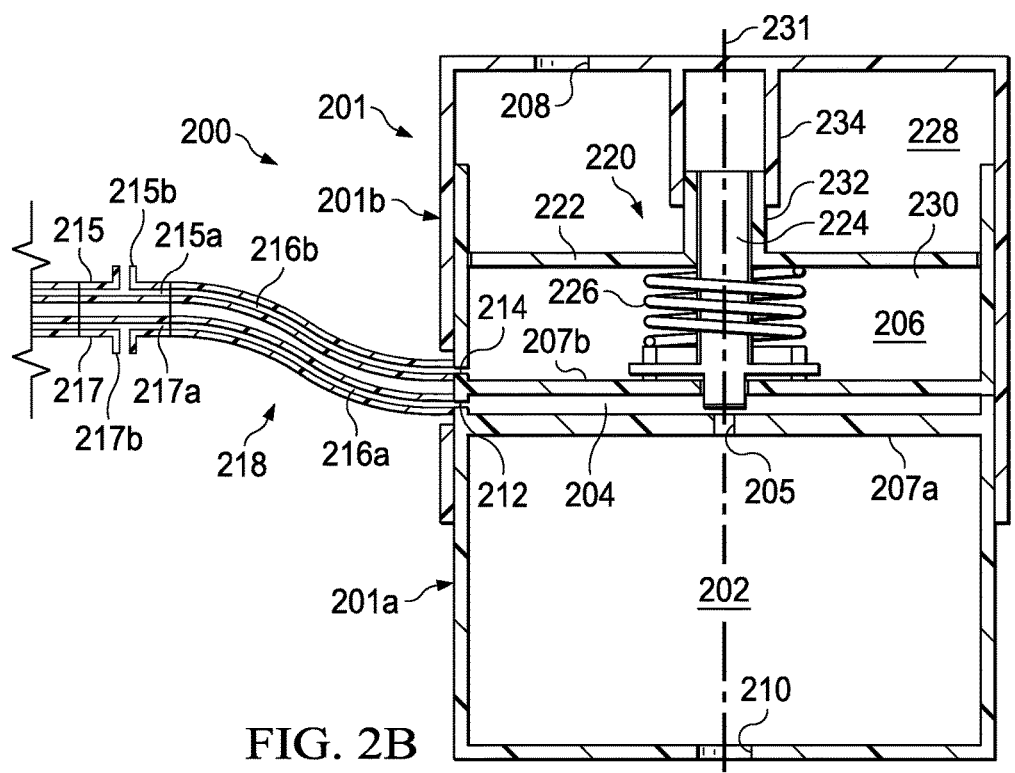

FIGS. 2A-2B are simplified schematic cross-sections illustrating details of an example embodiment of a regulator 200. The regulator 200 is an example embodiment of the regulator 106 in FIG. 1. As illustrated, the regulator 200 can include a housing 201 having a charging chamber 202, a supply chamber 204, and a control chamber 206. The charging chamber 202 may be fluidly coupled to the supply chamber 204 through a conduit, passage, or port, such as a charging port 205. A port 208 can provide fluid communication between the control chamber 206 and a source of ambient pressure. The charging chamber 202 may also include a port, such as a port 210, which can be fluidly coupled to a source of reduced pressure, such as the reduced-pressure source 104. The charging chamber 202 may be adapted to receive reduced pressure from a device that can be manually-actuated, or alternatively that can be powered by electrical or other means.

A supply port 212 may fluidly couple the supply chamber 204 to a dressing, such as the dressing 102 in FIG. 1. A control port 214 may fluidly couple the control chamber 206 to the dressing. For example, in one embodiment, a first lumen such as a supply lumen 216a, may fluidly connect the supply port 212 and the supply chamber 204 to a dressing. A second lumen, such as a feedback lumen 216b, may fluidly couple the control port 214 and the control chamber 206 to the dressing. In some embodiments, the supply lumen 216a and the feedback lumen 216b may be disposed within a single multi-lumen tube, such as a tube 218. In other embodiments, more than one tube may be used to couple a dressing to the supply port 212 and the control port 214.

A tee-fitting 215 may be coupled to the feedback lumen 216b. The tee-fitting 215 may have a first passage 215a and a second passage 215b. The first passage 215a and the second passage 215b may be perpendicular to and in fluid communication with one another. The first passage 215a may be fluidly coupled inline between the control chamber 206 and a dressing. For example, the first passage 215a may be fluidly coupled to the feedback lumen 216b. The second passage 215b may be fluidly coupled to another device, such as a pressure sensor, fluid source, or sampling device, for example. In some embodiments, a pressure sensor may be fluidly coupled to the second passage 215b and be in fluid communication with a control pressure in the control chamber 206.

A tee-fitting 217 may be coupled to the supply lumen 216a. The tee-fitting 215 may have a first passage 217a and a second passage 217b. The first passage 217a and the second passage 217b may be perpendicular to and in fluid communication with each other. At least one of the passages may be fluidly coupled inline between the supply chamber 204 and a dressing. For example, the first passage 217a may be fluidly coupled to the supply lumen 216a. The second passage 217b may be fluidly coupled to another device, such as a pressure sensor, fluid source, or sampling device, for example. In some embodiments, a pressure sensor may be fluidly coupled to the second passage 217b and be in fluid communication with a supply pressure in the supply chamber 204.

A regulator valve 220 can be operably associated with the charging port 205 to regulate fluid communication between the charging chamber 202 and the supply chamber 204. In some embodiments, the regulator valve 220 may include an actuator, a valve body, and an elastic member. An actuator can be a flexible or movable barrier, such as a piston 222. A valve body can be, for example, a generally rigid structure having a first end coupled to, adjoining, abutting, or otherwise engaging the piston 222, and movable with the piston, such as a stem 224. A second end of the valve body can be generally sized and shaped to engage and/or seal the charging port 205. In the illustrative embodiments, the stem 224 may extend through a partition into the supply chamber 204. An elastic member can be a spring, a rubber, or other elastic structure, such as a regulator spring 226, for example. The regulator spring 226 may be generally disposed between the piston 222 and the charging port 205. The regulator spring 226 can be disposed within the control chamber 206, but may be disposed in the supply chamber 204 in other embodiments. The regulator spring 226 in this embodiment may be a coil spring that is coaxial with the stem 224. The regulator spring 226 may bias the piston 222 against an ambient pressure 228 in the control chamber 206.

In some embodiments, the housing 201 may be formed from two components. For example, the housing 201 may be formed from a lower housing 201a and an upper housing 201b, as shown in the illustrative embodiments of FIGS. 2A-2B. In this example, the lower housing 201a and the upper housing 201b each include an end wall, a side wall adjoining the end wall, and an open end opposite the end wall. Either the lower housing 201a or the upper housing 201b may have an outside dimension less than an inside dimension of the other so that one may be inserted into the other to form a structure that provides a substantially closed interior. In some embodiments, the lower housing 201a and the upper housing 201b may be engaged to allow relative movement between them. In more particular embodiments, the lower housing 201a and the upper housing 201b may each have cylindrical side walls and rounded end walls.

The charging chamber 202 may be generally defined by adjoining walls of the housing 201, such as an end wall of the housing 201, a side wall or walls of the housing 201, and a partition within the housing 201, such as the chamber wall 207a. The supply chamber 204 may also be generally defined by adjoining walls within the housing 201. For example, the supply chamber 204 in FIGS. 2A-2B can be generally defined by the chamber wall 207a, a side wall or walls of the housing 201, and another partition, such as the chamber wall 207b. The control chamber 206 may be similarly described, for example, as a chamber defined by the chamber wall 207b, the side wall or walls of the housing 201, and another end wall of the housing 201. In this example embodiment, the charging chamber 202 and the supply chamber 204 may have a common wall, such as the chamber wall 207a, for example. The supply chamber 204 and the control chamber 206 may also have a common wall, such as the chamber wall 207b, for example. The charging chamber 202 and the supply chamber 204 may be fluidly isolated from each other except through the charging port 205. The charging chamber 202 and the supply chamber 204 may be fluidly isolated from the ambient environment. And the control chamber 206 may be fluidly isolated from the charging chamber 202 and the supply chamber 204.

The regulator valve 220 in this example can be disposed partially within the control chamber 206 and partially within the supply chamber 204, with circumferential edges of the piston 222 abutting or engaging the side wall or walls of the control chamber 206. The interface between the piston 222 and the walls of the control chamber 206 may also provide a fluid seal, dividing the control chamber 206 into a region of the ambient pressure 228 and a region of control pressure 230. However, the regulator valve 220 may also reciprocate within the control chamber 206 while maintaining the fluid seal. For example, the regulator valve 220 may additionally include flexible o-rings disposed between the piston 222 and the side wall of the control chamber 206, and the o-rings may be lubricated so that the regulator valve 220 can reciprocate within the control chamber 206.

In operation, pressure in the supply chamber 204 can be distributed to a remote chamber, environment, or other location through the supply port 212. For example, pressure in the supply chamber 204 may be distributed to a controlled environment, such as a sealed therapeutic environment associated with the reduced-pressure therapy system 100. The control pressure 230 in the control chamber 206 can be equalized with the pressure in the remote location through the control port 214. In reduced-pressure therapy applications, the control pressure 230 should be less than the ambient pressure 228, resulting in a pressure differential across the regulator valve 220. To simplify further description, the force on the regulator valve 220 resulting from the pressure differential on opposing sides of the piston 222 may be referred to as a "differential force." The regulator spring 226 also generally exerts a force on the regulator valve 220. In expected operating ranges, the force of the regulator spring 226 is directly proportional to a displacement of the ends of the regulator spring 226 from a relaxed state. Thus, if the control pressure 230 is less than the ambient pressure 228, the differential force on the piston 222 tends to compress the regulator spring 226 and, consequently, the force of the regulator spring 226 opposes the differential force. The differential force and the force of the regulator spring 226 can be combined to determine a net force acting on the regulator valve 220. The net force can cause the regulator valve 220 to move reciprocally within the control chamber 206, such as along a central axis 231 aligned with the charging port 205.

The regulator spring 226 may be selected, adjusted, modified, tuned, or otherwise calibrated so that the control pressure 230 must drop below a threshold value (such as a target pressure) before the net force can move the regulator valve 220 into a position that closes the charging port 205.

In some embodiments, for example, the piston 222 may rotate within the housing 201 to adjust the compression of the regulator spring 226. In the illustrative embodiments of FIGS. 2A-2B, the piston 222 includes a boss 232 that can be rigidly mated with a sleeve 234 of the upper housing 201b, and the stem 224 may be threaded or have a threaded portion engaged to the boss 232. The stem 224 may be locked radially with the housing 201 with a keyed feature. In such embodiments, the piston 222 and the sleeve 234 are generally locked radially, and compression of the regulator spring 226 may be adjusted by rotating the upper housing 201b, which can cause the piston 222 to rotate relative to the stem 224. The change in compression of the regulator spring 226 results in a change to the force of the regulator spring 226 acting on the regulator valve 220, and thus, a change in the threshold value of the control pressure 230 needed to actuate the regulator valve 220. In many applications, this threshold value of the control pressure 230 should generally correlate to a target pressure prescribed for reduced-pressure therapy, and may be referred to herein as the "therapy pressure" or "therapeutic pressure." Thus, in some embodiments, the therapy pressure may be adjusted by rotating the upper housing 201b. In yet more particular embodiments, the upper housing 201b may be calibrated to indicate various levels of the therapy pressure.

Thus, the charging chamber 202 may be charged to reduce the pressure in the charging chamber, and the pressure in the therapeutic environment may be regulated based on a differential between the therapy pressure and the control pressure 230. For example, the pressure may be regulated by balancing the force of the regulator spring 226 and a differential force. A differential force on the piston 222 may be produced by a pressure differential across the piston 222, such as the differential between the control pressure 230 on one side of the piston 222 and ambient pressure 228 on an opposing side of the piston 222, for example. For reduced-pressure therapy applications, the charging chamber 202 may be charged to a pressure lower than the therapy pressure. In some embodiments, for example, the desired therapy pressure may be about −125 mm Hg and pressure in the charging chamber 202 may be reduced to a pressure of about −150 mm Hg.

If the regulator valve 220 is calibrated to a particular therapy pressure and the control pressure 230 is higher than the therapy pressure, the force of the regulator spring 226 should exceed the differential force, and the net force should actuate the regulator valve 220, moving the regulator valve 220 into an open position (see FIG. 2B) in which the stem 224 disengages from the charging port 205. Disengagement of the stem 224 from the charging port 205 may also be referred to as opening the charging port 205. Pressure between the charging chamber 202 and the supply chamber 204 can equalize through the open charging port 205. As the pressure in the charging chamber 202 and the supply chamber 204 continues to equalize, the pressure in the supply chamber 204 continues to decrease. Unless there is a complete blockage in the fluid path between the supply chamber 204 and the therapeutic environment, pressure in the therapeutic environment also decreases and equalizes with the pressure in the supply chamber 204 through the supply lumen 216a. And unless there is a complete obstruction in the fluid path between the therapeutic environment and the control chamber 206, the control pressure 230 also decreases and equalizes with the pressure in the therapeutic environment through the feedback lumen 216b. As the control pressure 230 decreases and approaches the therapy pressure, the differential force increases until it exceeds the force of the regulator spring 226, causing the stem 224 to engage the charging port 205. Engagement of the stem 224 with the charging port 205 can substantially reduce or prevent fluid communication between the charging chamber 202 and the supply chamber 204 through the charging port 205, as shown in the illustrative embodiment of FIG. 2A. The engagement of the stem 224 with the charging port 205 may also be referred to as closing the charging port 205. The charging port 205 generally remains open until the control pressure 230 is less than or substantially equal to the therapy pressure. Advantageously, the regulator valve 220 can keep the charging port 205 open to compensate for pressure drops and partial blockages, particularly in the fluid path between the supply chamber 204 and a controlled environment, because pressure in the controlled environment can be directly measured by feedback lumen 216b.

Figure 3A:
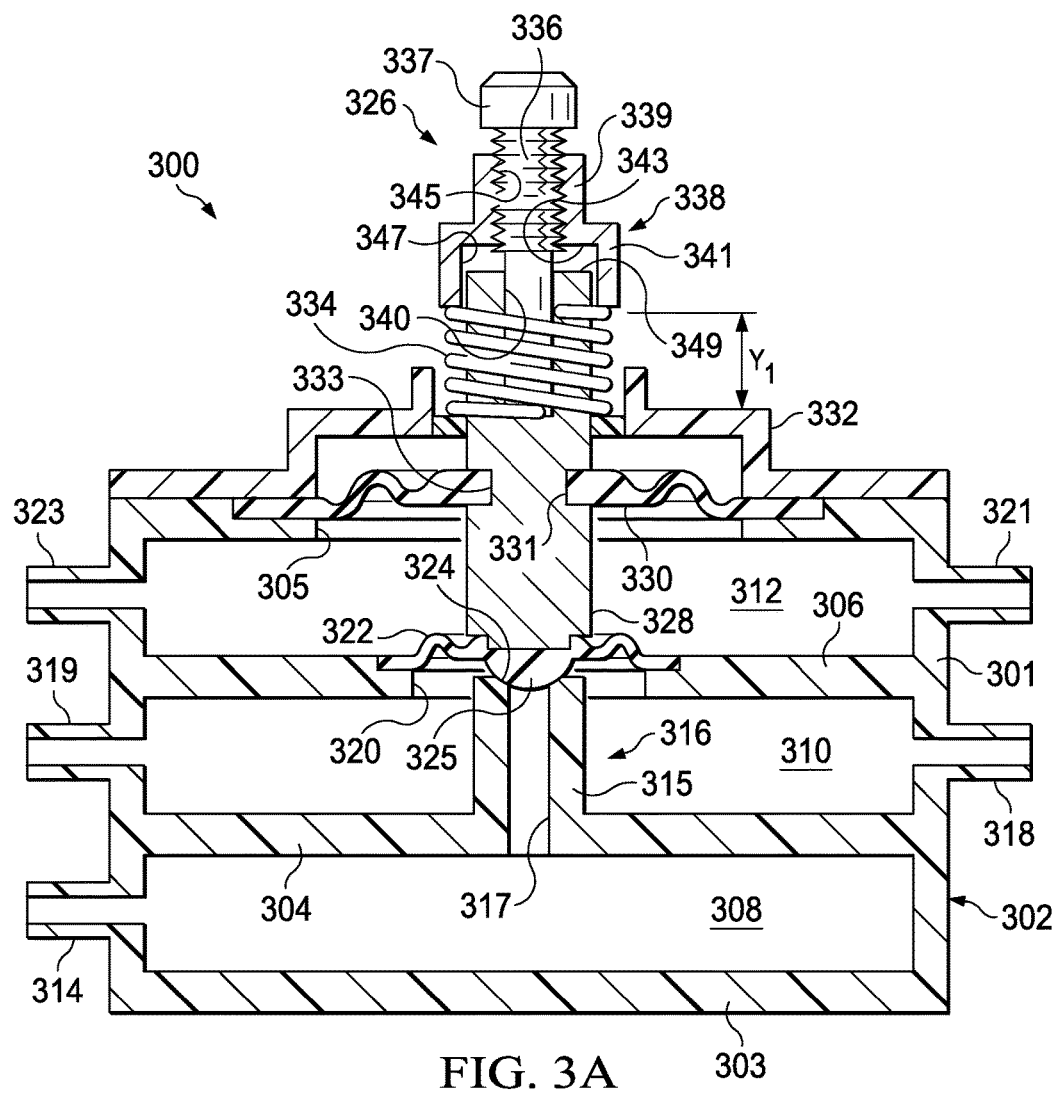
FIG. 3A is a schematic cross-section of another embodiment of a regulator for use with a reduced-pressure therapy system.

FIG. 3A is a cross-sectional view illustrating a regulator 300 that may be associated with some embodiments of the reduced-pressure therapy system 100. The regulator 300 is another example embodiment of the regulator 106. The regulator 300 may be similar to the regulator 200 of FIGS. 2A-2B in many respects, and may include a housing 302 and a regulator valve 326. The housing 302 may have an end wall 303, one or more side walls 301, and an open end 305 opposite the end wall 303. The side walls 301 may be coupled to peripheral portions of and generally perpendicular to the end wall 303.

The housing 302 may be partitioned by a first wall 304 and a second wall 306 to form a charging chamber 308, a supply chamber 310, and a control chamber 312. In the illustrative embodiment, the charging chamber 308 may adjoin the supply chamber 310, disposed between the end wall 303, the first wall 304, and the side walls 301. The supply chamber 310 may be disposed between the charging chamber 308 and the control chamber 312. For example, in FIG. 3A, the first wall 304 separates the charging chamber 308 and the supply chamber 310. The supply chamber 310 may be bounded by the first wall 304, the side walls 301, and the second wall 306. The control chamber 312 may adjoin the supply chamber 310, as shown in the illustrative embodiment of FIG. 3A. For example, the second wall 306 may separate the supply chamber 310 and the control chamber 312. The supply chamber 310 may be bounded by the second wall 306, the side walls 301, and the open end 305 of the housing 302. The first wall 304 and the second wall 306 may be coupled to the side walls 301 of the housing 302 at peripheral portions of the first wall 304 and the second wall 306. In some embodiments, no fluid communication may occur between the charging chamber 308, the supply chamber 310, and the control chamber 312 at the locations where the first wall 304 and the second wall 306 couple to the housing 302.

The housing 302, the first wall 304, and the second wall 306 may be formed of a material having a sufficient strength to resist collapse when a reduced pressure is supplied to the charging chamber 308, the supply chamber 310, and the control chamber 312, such as metals, hard plastics, or other suitable materials. For example, the housing 302, the first wall 304, and the second wall 306 may resist collapse when a reduced pressure of about 150 mm Hg (−150 mm Hg gauge pressure) is supplied to the charging chamber 308, the supply chamber 310, or the control chamber 312. In other exemplary embodiments, the housing 302, the first wall 304, and the second wall 306 may resist collapse when a reduced pressure of about 600 mm Hg (−600 mm Hg gauge pressure) is supplied to the charging chamber 308, the supply chamber 310, or the control chamber 312.

The charging chamber 308 may include a source port 314 and a charging port 316. The source port 314 may be disposed in one of the side walls 301 of the charging chamber 308 and may be fluidly coupled to the charging chamber 308. In the illustrative embodiment, the source port 314 may be configured to be fluidly coupled to a supply of reduced pressure, such as an electric pump, a manual pump, or wall-suction source, for example. In some embodiments, the source port 314 may be fluidly coupled to a wall-suction source by a conduit or tube. A one-way valve may be disposed in the source port 314 and oriented to prevent fluid flow into the charging chamber 308 through the source port 314 and permit fluid flow out of the charging chamber 308 through the source port 314.

In some embodiments, the charging port 316 may be disposed in the first wall 304, as shown in the illustrative embodiment of FIG. 3A. The charging port 316 may fluidly couple the charging chamber 308 and the supply chamber 310. In some embodiments, the charging port 316 may have a cylindrical wall 315 and a central passage 317 that extends between the charging chamber 308 and the supply chamber 310. The cylindrical wall 315 may include a portion extending into the supply chamber 310 from the first wall 304 so that the charging port 316 terminates near a center portion of the second wall 306. In some embodiments, the charging port 316 may be disposed in other locations of the first wall 304.

The supply chamber 310 may include a supply port 318 and a monitor port 319. In the illustrative embodiments, the supply port 318 may be fluidly coupled to the supply chamber 310 and provide an interface to the supply chamber 310. For example, the supply port 318 may be configured to be coupled to a tube, which can be coupled to a dressing or other upstream component. A one-way valve may be disposed in the supply port 318 and oriented to permit fluid flow into the supply chamber 310 through the supply port 318 and prevent fluid flow out of the supply chamber 310 through the supply port 318.

The monitor port 319 may also be fluidly coupled to the supply chamber 310, providing a second interface to the supply chamber 310. In some embodiments, for example, the monitor port 319 may be disposed in one of the side walls 301, opposite the supply port 318. In other embodiments, the monitor port 319 may be proximate to or adjacent to the supply port 318. The monitor port 319 may be fluidly coupled to a monitoring device, such as a sensor, indicator, or overpressure valve, for example. In some embodiments, the monitor port 319 may be capped so that no fluid communication may occur through the monitor port 319.

The control chamber 312 may include a control port 321 and a monitor port 323. In the illustrative embodiment, the control port 321 may be fluidly coupled to the control chamber 312 and provide an interface to the control chamber 312. In some embodiments, the control port 321 may be disposed on a same side of the regulator 300 as the supply port 318. In still other embodiments, the control port 321 may be vertically aligned with the supply port 318. In the illustrative embodiment of FIG. 3A, the control port 321 may be configured to be coupled to a tube, which can be coupled to a dressing or other upstream component. A one-way valve may be disposed in the control port 321 and oriented to prevent fluid flow into the control chamber 312 through the control port 321 and permit fluid flow out of the control chamber 312 through the control port 321.

The monitor port 323 may also be fluidly coupled to the control chamber 312. In some embodiments, the monitor port 323 may be opposite the control port 321. In other embodiments, the monitor port 323 may be disposed on a same side of the regulator 300 as the control port 321. In other embodiments, the monitor port 323 may be vertically aligned with the monitor port 319. The monitor port 323 may be fluidly coupled to a monitoring device, such as a sensor, indicator, or overpressure valve, for example. In some embodiments, the monitor port 323 may be capped so that no fluid communication may occur through the monitor port 323.

The second wall 306 may include an opening 320 in a center portion proximate to the distal end of the charging port 316. As illustrated in FIG. 3A, the opening 320 may be axially aligned with the central passage 317. The opening 320 may be larger than the distal end of charging port 316, providing a gap between a peripheral portion of the opening 320 and the distal end of the charging port 316. The gap provides a fluid path between the charging port 316 and the supply chamber 310. In some embodiments, the gap between the peripheral portion of the opening 320 and the distal end of the charging port 316 may be about 0.5 mm. In other embodiments, the gap between the peripheral portion of the opening 320 and the distal end of the charging port 316 may be less than 0.5 mm. In yet other alternative or additional embodiments, the distal end of the charging port 316 may be vertically separated from the second wall 306. For example, the distal end of the charging port 316 may be vertically separated from a lower surface of the second wall 306 a distance of about 0.5 mm. In other embodiments, the distance separating the distal end of the charging port 306 and the lower surface of the second wall 306 may be greater than 0.5 mm.

The regulator valve 326 can be operably associated with the charging port 316 to regulate fluid communication between the charging chamber 308 and the supply chamber 310. The regulator valve 326 can be biased to either open or close the charging port 316. In some embodiments, the regulator valve 326 may be coupled to the open end 305 of the housing 302, as illustrated in FIG. 3A. The regulator valve 326 may be coupled to ends of the side walls 301 of the housing 302, opposite the end wall 303 of the housing 302. In some embodiments, the regulator valve 326 may substantially limit or prevent fluid communication through the open end 305 of the housing 302. The regulator valve 326 may include a valve member 322, a valve body, such as a stem 328, and an actuator 330. The regulator valve 326 may also include a regulator cap 332, a regulator spring 334, an adjustment shaft 336, and a tension adjuster, such as a push button, a lever, or a dial 338.

Figure 3B:
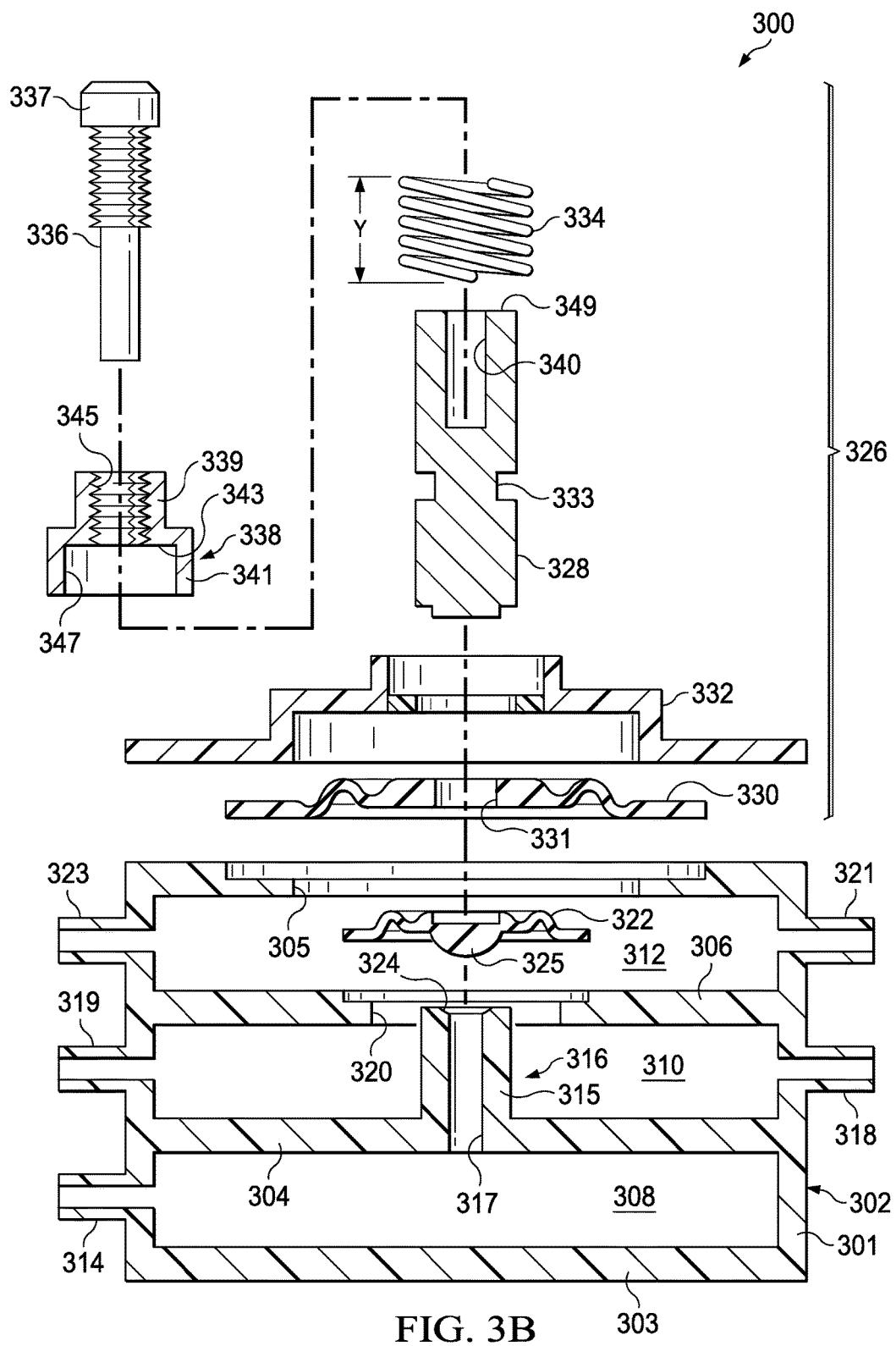
FIG. 3B is a schematic exploded view of the regulator of FIG. 3A.

FIG. 3B is a schematic sectional assembly view of the regulator 300 illustrating additional details that may be associated with some embodiments. In some embodiments, the valve member 322 may be a flexible membrane, such as a diaphragm. In some embodiments, the valve member 322 may have a generally disc-like shape with a diameter larger than the diameter of the opening 320 in the second wall 306. In other embodiments, the valve member 322 may have a shape matched to a shape of the opening 320, for example, square, rectangular, ovoid, triangular, or amorphous shapes. The valve member 322 may have peripheral portions coupled to the second wall 306, and the valve member 322 may extend across the opening 320. When the valve member 322 is coupled to the second wall 306, the valve member 322 may fluidly isolate the control chamber 312 from the supply chamber 310. For example, a difference in the pressures in the supply chamber 310 and the control chamber 312 may cause deflection of the valve member 322. In some embodiments, the valve member 322 may be formed from a silicone material. In some embodiments, the valve member 322 may have a hardness rating between about 30 Shore A and about 50 Shore A.

As illustrated in FIG. 3B, some embodiments of the charging port 316 may have a valve seat 324 on the distal end. The valve seat 324 may provide a tapered or beveled edge proximate to the central passage 317 of the charging port 316. In some embodiments, the valve member 322 may include an enlarged portion 325 configured to engage the valve seat 324. For example, the valve member 322 may be positioned so that the enlarged portion 325 of the valve member 322 may engage a beveled edge of the valve seat 324 of the charging port 316 in a closed position. If engaged in such a manner, can substantially prevent fluid communication through the passage 317 of the charging port 316.

The stem 328 may be cylindrical and have an end coupled to the valve member 322. In some embodiments, a first end of the stem 328 may be coupled to the enlarged portion 325 of the valve member 322. The stem 328 is elongated so that the stem 328 may extend through the open end 305 when the end of the stem 328 is coupled to the valve member 322. A second end of the stem 328 may include a cavity 340. The cavity 340 may be a recess into the stem 328 from the second end of the stem 328. The cavity 340 may have a diameter less than a diameter of the stem 328 so that a shoulder 349 may be formed at the end of the stem 328 adjacent to an opening of the cavity 340. The shoulder 349 may face away from the housing 302. The stem 328 may also have a recess 333 disposed between ends of the stem 328. In some embodiments, the recess 333 is annular and may be disposed proximate to a center of a length of the stem 328.

The actuator 330 may be coupled to the housing 302 so that the actuator 330 covers the open end 305. In some embodiments, the actuator 330 extends across the open end 305 to fluidly isolate the control chamber 312 from the ambient environment. In some embodiments, the actuator 330 may be a diaphragm having peripheral portions coupled to the ends of the side walls 301 of the housing 302. The actuator 330 may have an elasticity permitting a center portion of the actuator 330 to deflect from an equilibrium position while the peripheral portions of the actuator 330 remain affixed to the housing 302. In some embodiments, the actuator 330 may be formed of an elastomeric material. For example, the actuator 330 may be formed of a silicone. In some embodiments, the actuator 330 may be formed from a material having a hardness rating between about 30 Shore A and about 50 Shore A.

The actuator 330 may have an opening 331 proximate to a center portion of the actuator 330. The opening 331 may receive the stem 328 so that the stem 328 extends through the actuator 330. In some embodiments, the actuator 330 may be coupled or otherwise sealed to the stem 328. For example, the actuator 330 may be welded to the stem 328 at the opening 331. For example, at least a portion of the actuator 330 adjacent the opening 331 may be inserted into the recess 333 to couple the actuator 330 to the stem 328. In some embodiments, movement of the stem 328 along an axis of the stem 328 causes movement of the center portion of the actuator 330, and movement of the actuator 330 along an axis of the stem 328 may cause movement of the stem 328.

When assembled, as shown in FIG. 3A, the regulator cap 332 may be coupled to the housing 302 so that the regulator cap 332 is adjacent to the control chamber 312 and the open end 305. In the illustrative embodiments, the regulator cap 332 covers the open end 305 of the housing 302 and includes a raised portion extending away from the control chamber 312 near a center of the regulator cap 332. In some embodiments, the raised portion may be coextensive with the open end 305 so that the regulator cap 332 may be separated from the actuator 330 near the open end 305. The stem 328 may extend through the raised portion of the regulator cap 332. The regulator cap 332 may be sealed to the stem 328. In some embodiments, the stem 328 may move relative to the regulator cap 332 while remaining sealed to the regulator cap 332. In other embodiments, the stem 328 may not be fluidly sealed to the regulator cap 332 so that an ambient pressure adjacent an exterior of the regulator cap 332 may be substantially equivalent to a pressure in the area between the raised portion of the regulator cap 332 and the actuator 330.

The regulator spring 334 may be disposed on the stem 328 so that the regulator spring 334 circumscribes the stem 328. The regulator spring 334 may have a first end adjacent to the regulator cap 332. In some embodiments, the first end of the regulator spring 334 may contact the regulator cap 332 so that the regulator spring 334 may be compressed against the regulator cap 332. A second end of the regulator spring 334 may be adjacent to the end of the stem 328 that has the cavity 340 disposed therein. The regulator spring 334 may have a length Y in a relaxed position, as shown in FIG. 3B. In the relaxed position, the regulator spring 334 may be neither extended nor compressed so that the regulator spring 334 does not exert a spring force. In some embodiments, a length Y1 may be the length of the regulator spring 334 in a compressed position, as shown in FIG. 3A, for example if the regulator valve 326 blocks fluid communication through the charging port 316.

The adjustment shaft 336 may have an end disposed within the cavity 340 and may be coupled to the stem 328 so that the adjustment shaft 336 and the stem 328 can move as integral members. The adjustment shaft 336 may be cylindrical and have an enlarged distal end forming an adjustment cap 337 of the adjustment shaft 336. A portion of the adjustment shaft 336 may be threaded between the adjustment cap 337 and the end disposed within the cavity 340. In some embodiments, the adjustment shaft 336 may be threaded between the adjustment cap 337 and an opening of the cavity 340 of the stem 328.

The dial 338 may be a tubular body having a first portion 339 and a second portion 341. The first portion 339 may have a cavity 345, and the cavity 345 has a width or diameter substantially equal to the outer diameter of the threaded portion of the adjustment shaft 336. The second portion 341 may also have a cavity 347, the width or diameter of the cavity 347 may be substantially equal to the outer diameter of the stem 328. The first portion 339 and the second portion 341 are preferably joined, in the illustrative embodiments of FIG. 3A, forming a shoulder 343 between the cavity 345 and the cavity 347. The dial 330 can be disposed on the stem 328 so that the shoulder 343 faces the cavity 340. As shown in the illustrative embodiment of FIG. 3A, the shoulder 343 may have an annular width substantially equal to the width of a shoulder 349 of the stem 328 formed by the cavity 340. The dial 338 may be moveably coupled to the adjustment shaft 336 proximate to the adjustment cap 337 of the adjustment shaft 336. In some embodiments, the first portion 339 of the dial 338 is adjacent to the adjustment cap 337 of the adjustment shaft 336. In some embodiments, the surface of the cavity 345 of the first portion 339 may be threaded. The dial 338 may be threaded to the adjustment shaft 336, allowing the dial 338 to be rotated about the adjustment shaft 336. Rotation of the dial 338 about the adjustment shaft 336 may cause the dial 338 to move parallel to an axis of the adjustment shaft 336. In this manner, the dial 338 may be moved along the adjustment shaft 336.

Figure 3C:
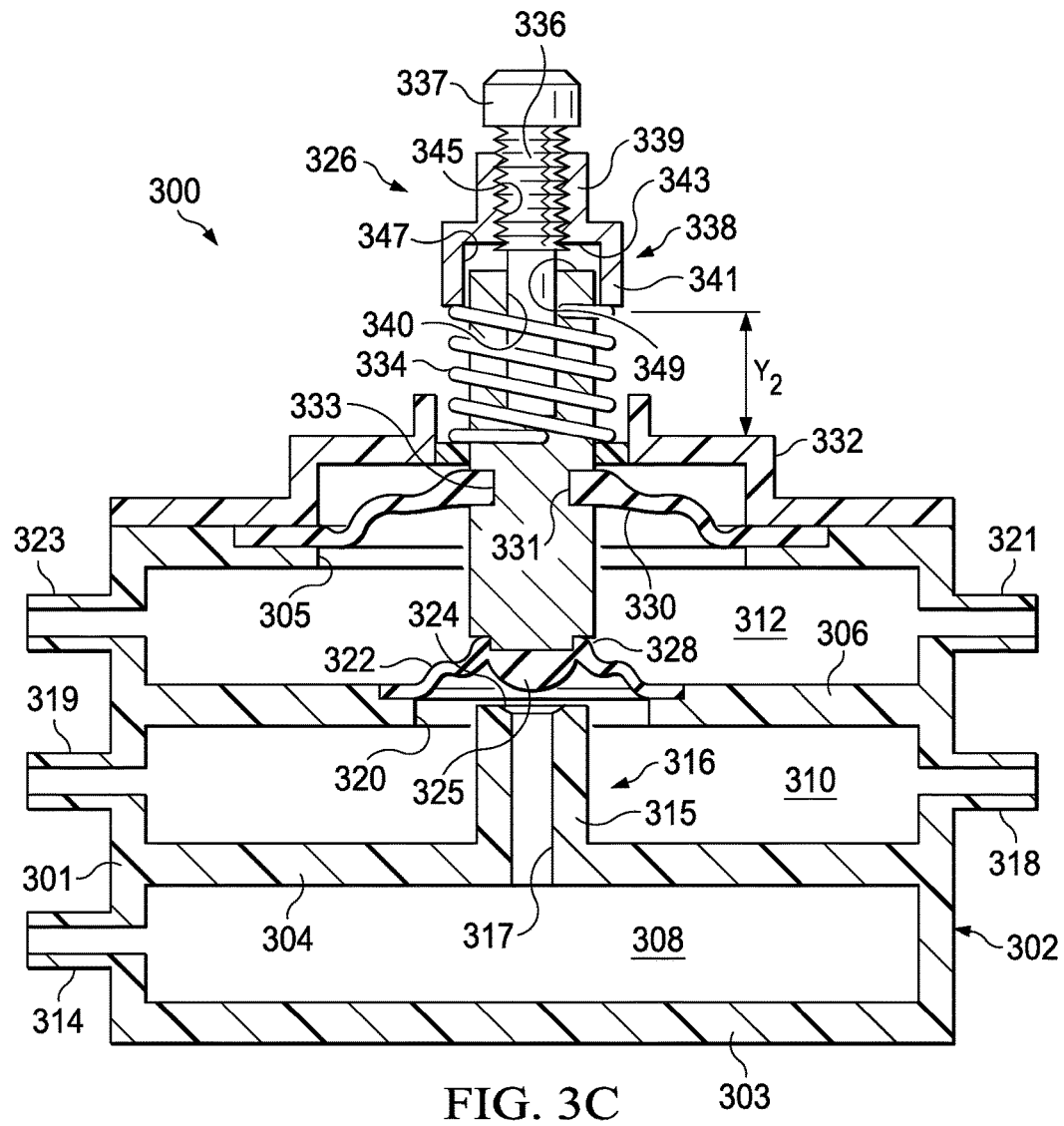
FIG. 3C is a schematic cross-section of the regulator of FIG. 3A having a regulator valve in an open position.

FIG. 3C is a schematic sectional view of the regulator 300 illustrating additional details that may be associated with some embodiments of the regulator 300 in an open position. The dial 338 may be positioned on the adjustment shaft 336 so that an end of the second portion 341 of the dial 338 contacts the distal end of the regulator spring 334. For example, the dial 338 may be threaded onto the adjustment shaft 336, and additional rotation of the dial 338 relative to the adjustment shaft 336 may move the dial 338 axially closer to the regulator cap 332 to compress the regulator spring 334. Compression of the regulator spring 334 by the dial 338 shortens the length of the regulator spring 334. This compression may cause the regulator spring 334 to exert a force on the dial 338 urging the dial 338 away from the regulator cap 332. In some embodiments, the regulator spring 334 may have a length Y2 if the regulator spring 334 is compressed by the dial 338. The force exerted by the regulator spring 334 is directly proportional to the displacement of the regulator spring 334 from the relaxed position. The force exerted by the regulator spring 334 on the dial 338 similarly urges the adjustment shaft 336, the coupled stem 328, and the coupled valve member 322 upward. In the illustrative embodiment, the force also urges the valve member 322 away from the charging port 316 into an open position. In the open position, fluid communication may occur through the charging port 316.

A differential force may also operate on the actuator 330. The differential force may be a force generated by a difference in pressures between the control chamber 312 and the ambient environment of the regulator 300. The pressure in the control chamber 312 may also be referred to as a control pressure. If the control pressure in the control chamber 312 and the pressure in the ambient environment are substantially equal, the differential force may be approximately zero. If the control pressure in the control chamber 312 is less than the ambient pressure, for example, if the regulator 300 is being used to provide reduced-pressure therapy, the differential force may act to urge the actuator 330, the coupled stem 328, and the valve member 322 toward the distal end of the charging port 316.

If the differential force is greater than the force of the regulator spring 334 acting on the stem 328, the valve member 322 may be urged into contact with the distal end of the charging port 316 to prevent fluid communication through the charging port 316 in a closed position, as shown in FIG. 3A. If the differential force is less than the force on the regulator spring 334, the valve member 322 may be urged away from the distal end of the charging port 316 to permit fluid communication through the charging port 316 in the open position, shown in FIG. 3C. The dial 338 can be threaded down the adjustment shaft 336 to control the compression of the regulator spring 334 from the relaxed length Y. Thus, the compression of the regulator spring 334 can be controlled to select a prescribed therapy, so that the force of the regulator spring 334 may be overcome when the therapy pressure is reached in the control chamber 312.

In other embodiments, a differential force may act on the valve member 322. For example, the supply pressure in the supply chamber 310 may exert a force on the valve member 322, and the control pressure in the control chamber 312 may exert a force on the valve member 322. The sum of the forces acting on the valve member 322 may be referred to as a valve force. The valve force may urge the valve member 322 into or out of contact with the charging port 316. In some embodiments, the valve force may act in opposition to the differential force acting on the actuator 330. The relative dimensions of the valve member 322 and the actuator 330 may be selected so that the actuator 330 is several times larger than the valve member 322. For example, the actuator 330 may have a major dimension that is greater than a corresponding dimension of the valve member 322. In some embodiments, the actuator 330 may have a diameter that is greater than a diameter of the valve member 322. A large difference in size between the actuator 330 and the valve member 322 correlates to a similarly large difference in the surface areas of the actuator 330 and the valve member 322. The larger surface area of the actuator 330 allows the differential force acting on the actuator 330 to act over a larger area than the valve force acting on the valve member 322. As a result, the differential force acting on the actuator 330 may overcome other forces acting on other components of the regulator 300, such as the valve member 322, allowing the actuator 330 to control the movement of the stem 328. In some embodiments, the opening 320 may be made smaller than depicted, and the charging port 316 may be further separated from the lower surface of the second wall 306. In such an embodiment, the valve member 322 may be made relatively smaller so that the valve force acts on a smaller surface area than the differential force.

Reduced-Pressure Therapy System

Figure 4:
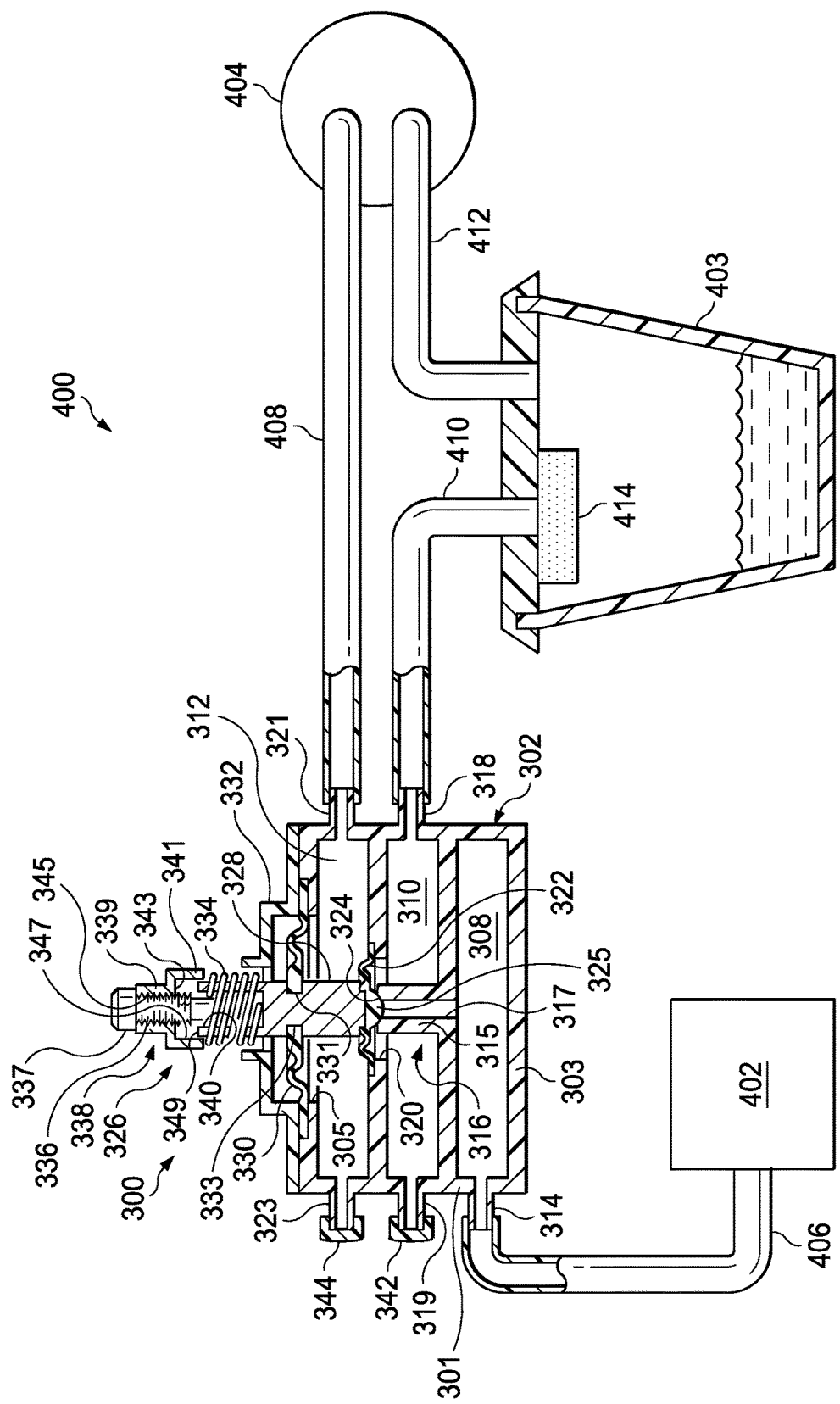
FIG. 4 is a schematic cross-section of an example embodiment of a reduced-pressure therapy system using the regulator of FIG. 3A.

FIG. 4 is a schematic illustration of a reduced-pressure system 400 illustrating additional details that may be associated with the operation of the regulator 300. The reduced-pressure system 400 is an example embodiment of the reduced-pressure system 100. The reduced-pressure system 400 includes a reduced-pressure source 402, a container 403, and a dressing 404. The reduced-pressure source 402 may be a wall-suction source, a manual pump, or an electric pump, for example. In the illustrative embodiment, the reduced-pressure source 402 may be a wall-suction source, and may be fluidly coupled to the source port 314. For example, a tube 406 may fluidly couple the reduced-pressure source 402 to the source port 314, as shown in the illustrative embodiment of FIG. 4. The container 403 is an example embodiment of the container 112, and may be fluidly coupled to the supply port 318. In some embodiments, for example, a tube 410 may fluidly couple the container 403 to the supply port 318. The container 403 may include a filter, such as a hydrophobic filter 414 adjacent to an end of the tube 410. The dressing 404 is an example embodiment of the dressing 102, and may be fluidly coupled to the container 403. For example, a tube 412 may fluidly couple the dressing 404 to the container 403. The dressing 404 may have a pressure that may also be referred to as a manifold pressure. In some embodiments, the tube 410 and the tube 412 may each have at least one lumen. The at least one lumen in the tube 410 and the tube 412 may collectively be referred to as a supply lumen. In other embodiments, the container 403 may be omitted, and the tube 410 may be coupled directly to the dressing 404. In these embodiments, the at least one lumen in the tube 410 may be considered a supply lumen. The dressing 404 may also be fluidly coupled to the control port 321. For example, a tube 408 may fluidly couple the dressing 404 to the control port 321. In some embodiments, the tube 408 may have at least one lumen. The at least one lumen of the tube 408 may also be referred to as a feedback lumen.

The dressing 404 may be fluidly coupled to the supply port 318 and the control port 321 so that fluid communication may occur between the supply chamber 310 and the dressing 404 through the container 403, and between the dressing 404 and the control chamber 312. Fluid communication between the dressing 404, the supply chamber 310 and the control chamber 312 may equalize the pressures in the supply chamber 310, the dressing 404, and the control chamber 312. For example, fluid communication between the dressing 404, the supply chamber 310, and the control chamber 312 may equalize the supply pressure in the supply chamber 310, the manifold pressure in the dressing 404, and the control pressure in the control chamber 312. If the source port 314 is not coupled to the reduced-pressure source 402, the charging port 316 may remain open and the ambient pressure may equalize between the charging chamber 308, the supply chamber 310, the dressing 404, and the control chamber 312.

The reduced-pressure source 402 may be coupled to the source port 314, providing a reduced pressure to the charging chamber 308. If the regulator valve 326 is in the open position, the charging port 316 provides a fluid path between the charging chamber 308 and the supply chamber 310. As the supply of reduced pressure reduces the pressure within the charging chamber 308, the pressure in the supply chamber 310 may similarly drop. The pressure in the supply chamber 310 may also be referred to as a supply pressure. Fluid communication through the supply port 318 will similarly lower the pressure in the dressing 404, and fluid communication through the control port 321 may similarly begin to lower the pressure in the control chamber 312. As the control pressure in the control chamber 312 drops, the differential force, acting in opposition to the force of the regulator spring 334 will increase, eventually overcoming the force of the regulator spring 334, causing the stem 328 to move downward and forcing the regulator valve 326 into the closed position in which the valve member 322 is seated in the charging port 316. In the closed position, the valve member 322 may block fluid communication through the charging port 316. Decreases in reduced pressure at the dressing 404 may decrease the differential force, so that the biasing force of the regulator spring 334 overcomes the differential force to open the regulator valve 326. In the open position, fluid communication through the charging port 316 may resume until the pressure at the dressing 404, and in turn the control chamber 312, drops sufficiently to overcome the regulator spring 334, again closing the regulator valve 326.

Repeated opening and closing of the regulator valve 326 may occur while reduced-pressure therapy is provided.

Feedback Systems

FIG. 5 is a schematic view illustrating an example embodiment of a feedback system 500 that may be used with some embodiments of the reduced-pressure therapy system 400. In FIG. 5, for example, the feedback system is illustrated with an example embodiment of the regulator 300. In some embodiments, the feedback system 500 may include a printed circuit board 502 having a pressure sensor 504 disposed thereon. The printed circuit board 502 may be an electronic device having one or more electronic components communicatively coupled by conductive pathways 503. Generally, printed circuit boards may be formed of conductive and non-conductive laminar sheets that are chemically etched to create communicative couplings. Printed circuit boards may also include additional electronic components such as capacitors, resistors, or other active devices. In some embodiments, the printed circuit board 502 may include a power supply or electric potential source, such as a battery 506, and a signal interface or indicator. In some embodiments, the signal interface may be a visual device, such as a light emitting diode (LED) 508, an auditory device, such as a speaker or auditory pulse emitter, a tactile device, such as a moving protrusion, or an olfactory device. The printed circuit board 502 may further include an electronic storage device, such as a memory, a processing unit, and other devices configured to operate the feedback system 500.

The pressure sensor 504 may be an electronic device communicatively coupled to the printed circuit board 502, the LED 508, and the battery 506. In some embodiments, the pressure sensor 504 may be a piezoresistive strain gauge, a capacitive sensor, an electromagnetic sensor, a piezoelectric sensor, an optical sensor, or a potentiometric sensor, for example. The pressure sensor 504 can measure a strain caused by an applied pressure. The pressure sensor 504 may be calibrated by relating a known amount of strain to a known pressure applied. The known relationship may be used to determine an unknown applied pressure based on a measured amount of strain. In some embodiments, the pressure sensor 504 may include a receptacle configured to receive an applied pressure. In the illustrated embodiment, the pressure sensor 504 may be fluidly coupled to the monitor port 323 of the regulator 300 by a tube 510.

The LED 508 may be a semiconductor light source that includes a chip of semiconducting material that is doped with impurities to create a p-n junction. Current may be supplied to the p-n junction, causing movement of electrons across the junction and the release of energy in the form of a photon. The photon may comprise visible light having a particular wavelength. The wavelength of the photons emitted by the LED 508 may be selected during manufacturing of the LED 508 so that the LED 508 may emit a desired color of light. In some embodiments, the LED 508 may be formed on the printed circuit board 502. In other embodiments, the LED 508 may be formed independently and later communicatively coupled to the printed circuit board 502. The LED 508 may be communicatively coupled to the pressure sensor 504 to receive a signal from the pressure sensor 504 in response to an applied pressure.

The battery 506 may be a single-cell voltage source that may be coupled to the printed circuit board 502. In some embodiments, the battery 506 may be replaceable. In other embodiments, the battery 506 may be rechargeable and configured to receive a current or voltage from an external source. The battery 506 may be further communicatively coupled to the LED 508 and the pressure sensor 504 to provide current to the LED 508 and the pressure sensor 504 for the operation thereof.

In operation, the feedback system 500 may be fluidly coupled to the regulator 300 to determine pressures in the chambers of the regulator 300 and indicate an operating state of the regulator 300 in response. In some embodiments, the operating state of the regulator 300 can include a current pressure, a pressure differential, a leak condition, a blockage condition, a canister full condition, or an overpressure condition, for example.

In some embodiments, the pressure sensor 504 may be fluidly coupled to the control chamber 312. For example, the pressure sensor 504 may be fluidly coupled to the tube 510 that may be fluidly coupled to the monitor port 323. A reduced pressure may be supplied to the charging chamber 308, and the regulator 300 may operate as described above to control delivery of reduced-pressure therapy. The control pressure in the control chamber 312 may be fluidly communicated to the pressure sensor 504 through the tube 510. The pressure sensor 504 may determine an amount of strain caused by the control pressure applied to the pressure sensor 504 through the tube 510. The pressure sensor 504 may determine a value of the control pressure based on the measured strain.

The feedback system 500 may provide a signal for one or more operating states. For example, the feedback system 500 may provided a generic alarm for a leakage condition, a blockage condition, or a canister full condition. In another example, the feedback system 500 may illuminate the LED 508 if the pressure sensor 504 measures a control pressure within a therapeutic range of the therapy pressure. In some embodiments, the therapy pressure may be a pressure of about −120 mm Hg, for example, and the therapeutic range may have a tolerance of about 10 mm Hg above or below the therapy pressure. As used herein, a pressure exceeding an upper limit of the therapeutic range refers to a reduced pressure that is greater than the therapeutic range. For example, if the therapy pressure is −120 mm Hg, the upper limit of the therapeutic range is −130 mm Hg, and a reduced pressure of −131 mm Hg would exceed the upper limit of the therapeutic range. Similarly, as used herein, a pressure exceeding a lower limit of the therapeutic range refers to a reduced pressure that is less than the therapeutic range. For example, if the therapy pressure is −120 mm Hg, the lower limit of the therapeutic range is −110 mm Hg, and a reduced pressure of −109 mm Hg would exceed the lower limit of the therapeutic range.

In some embodiments, if the control pressure determined by the pressure sensor 504 is within the therapeutic range of the therapy pressure, a signal may be communicated to the LED 508, causing the LED 508 to illuminate. The illumination of the LED 508 may continue so long as the control pressure in the control chamber 312 is within the therapeutic range. If the control pressure in the control chamber 312 exceeds the upper limit or the lower limit of the therapeutic range, the feedback system 500 may no longer illuminate the LED 508. In this manner, the feedback system 500 may signal an operating state of the reduced-pressure therapy system 400 is an application of the therapy pressure.

In some embodiments, if the pressure communicated to the pressure sensor 504 through the tube 510 is within the therapeutic range of the therapy pressure, the pressure sensor 504 may generate a signal that completes an electrical circuit on the printed circuit board 502. Completion of the electrical circuit may provide current to the LED 508, causing the LED 508 to illuminate. In other embodiments, if the pressure communicated to the pressure sensor 504 through the tube 510 is within the therapeutic range of the therapy pressure, the pressure sensor 504 may generate a signal that interrupts an electrical circuit on the printed circuit board 502. In this embodiment, interruption of the circuit may prevent current from reaching the LED 508 so that the LED 508, which may have been illuminated, will cease illumination.

In some embodiments, the therapy pressure may be selected during the manufacturing of the feedback system 500. For example, the therapy pressure may be hardwired to the printed circuit board 502. In other embodiments, the printed circuit board 502 may include a controller or central processing unit having the therapy pressure programmed into the controller or central processing unit. In other embodiments, the feedback system 500 may include an input device, such as a switch, a dial, or a keyboard, for example, that may permit an operator to input the therapy pressure.

In still other embodiments, the LED 508 may be capable of illumination in multiple wavelengths so that different colors may be illuminated in response to different control pressures determined by the pressure sensor 504. In these embodiments, the colors may be coordinated to a particular control pressure determined by the pressure sensor 504 so that the LED 508 may provide a greater range of information outside of whether or not the control pressure is within the therapeutic range of the therapy pressure. In some embodiments, the LED 508 may include multiple LEDs, such as a green LED, a blue LED, and a red LED. For example, the feedback system 500 may illuminate a red LED if the control pressure determined by the pressure sensor 504 exceeds the upper limit of the therapeutic range of the therapy pressure, indicating an overpressure condition. The feedback system 500 may illuminate a blue LED if the pressure determined by the pressure sensor 504 exceeds a lower limit of the therapeutic range of the therapy pressure, indicating a leak condition. The feedback system 500 may illuminate a green LED if the pressure determined by the pressure sensor 504 is within the therapeutic range of the therapy pressure, indicating an application of reduced-pressure therapy. In other embodiments, the LED 508 may be capable of selectively emitting light having a blue tone, a red tone, a green tone, or other colors.

In still other embodiments, the regulator 300 may include a potentiometer 512 communicatively coupled to the adjustment shaft 336 and the dial 338. The potentiometer 512 may be a three-terminal resistor, for example, with a sliding contact that forms an adjustable voltage divider. The potentiometer 512 may provide a variable voltage in response to operation of the sliding contact. In some embodiments, the potentiometer 512 may be calibrated to provide a voltage signal that corresponds to the axial position of the dial 338 relative to the adjustment shaft 336. When the dial 338 is moved relative to the adjustment shaft 336, the voltage signal provided by the potentiometer 512 may change. In some embodiments, the voltage signal provided by the potentiometer 512 may be related to the therapy pressure. In these embodiments, the potentiometer 512 may be further communicatively coupled to the printed circuit board 502. The voltage signal received by the printed circuit board 502 may be recorded as the therapy pressure so that the feedback system 500 may adjust operation of the LED 508 in response to a change in therapy pressure. For example, if the dial 338 is positioned so that a therapy pressure of about −120 mm Hg may be desired, the voltage signal communicated to the printed circuit board 502 may cause the feedback system 500 to adjust operation of the LED 508 so that the LED 508 may not illuminate until the pressure sensor 504 determines that a control pressure of about −120 mm Hg has been communicated through the tube 510. If the dial 338 is then positioned so that a therapy pressure of −110 mm Hg may be desired, the voltage signal communicated to the printed circuit board 502 by the potentiometer 512 may cause the feedback system 500 to adjust operation of the LED 508 so that the LED 508 may not illuminate until the pressure sensor 504 determines that a control pressure of about −110 mm Hg has been communicated through the tube 510.

In some embodiments, the printed circuit board 502 may include a power button that may selectively provide voltage or potential to the printed circuit board 502. In some embodiments, the power button may be an electric switch that, if open, interrupts a circuit on the printed circuit board 502. In other embodiments, the power button may take the form of a pull tab positioned between the battery 506 and a contact terminal on the printed circuit board 502. If the pull tab is removed, a circuit on the printed circuit board 502 may be completed through the battery 506.

The printed circuit board 502 may further include a speaker communicatively coupled to the printed circuit board 502 and the battery 506. In these embodiments, the signal may be an audible alarm. If the pressure changes by a predetermined amount, the printed circuit board 502 may supply the speaker with a current to cause the speaker to provide an audible alarm. In some embodiments, the printed circuit board 502 may include an audio pause button. The audio pause button may permit the audio capability of the printed circuit board 502 to be muted.

In other embodiments, the feedback system 500 may be used with the regulator 200. For example, the pressure sensor 504 may be fluidly coupled to the control chamber 206 of the regulator 200. In some embodiments, the pressure sensor 504 may be fluidly coupled to the tee-fitting 215. The tee-fitting 215 may provide fluid communication between the pressure sensor 504 and the control chamber 206. The feedback system 500 may operate with the regulator 200 as described above with respect to the regulator 300.

FIG. 6 is a schematic view illustrating additional details of another example embodiment of a feedback system 600 that may be used with some embodiments of the reduced-pressure therapy system 400. In FIG. 6, for example, the feedback system 600 is illustrated with an example embodiment of the regulator 300. The feedback system 600 may include a printed circuit board 602 having a control pressure sensor 604 and a supply pressure sensor 614 disposed thereon. The printed circuit board 602 may be similar to the printed circuit board 502 of FIG. 5 in many respects, and may include conductive pathways 603 communicatively coupling electric components as described above. In the illustrative embodiment of FIG. 6, the printed circuit board 602 may also include a power supply or electric potential source, such as a battery 606, and a signal interface or indicator, such as a liquid crystal display (LCD) 608. In some embodiments, the signal interface may be a visual device, such as a light or the like, an auditory device, such as a speaker or auditory pulse emitter, a tactile device, such as a moving protrusion, or an olfactory device. The printed circuit board 602 may further include an electronic storage device, such as a memory, a processing unit, and other devices configured to operate the feedback system 600.

The control pressure sensor 604 may be an electronic device communicatively coupled to the printed circuit board 602, the LCD 608, and the battery 606. The control pressure sensor 604 may be similar to and operate as described above with respect to the pressure sensor 504 of FIG. 5. In the illustrated embodiment of FIG. 6, the control pressure sensor 604 may be fluidly coupled to the monitor port 323 of the regulator 300 by a tube 610.

The supply pressure sensor 614 may be an electronic device communicatively coupled to the printed circuit board 602, the LCD 608, and the battery 606. The supply pressure sensor 614 may be similar to and operate as described above with respect to the pressure sensor 504 of FIG. 5. In the illustrated embodiment of FIG. 6, the supply pressure sensor 614 may be fluidly coupled to the monitor port 319 of the regulator 300 by a tube 616.

The battery 606 may be similar to and operate as described above with respect to the battery 506 of FIG. 5. In the illustrative embodiment of FIG. 6, the battery 606 is further communicatively coupled to the LCD 608, the control pressure sensor 604, and the supply pressure sensor 614 to provide electric power to the LCD 608 and the control pressure sensor 604 for the operation thereof.

The LCD 608 may be a display that presents images using the light-modulating properties of liquid crystals. In general, an LCD includes a layer of molecules aligned between two electrodes and two polarizing filters. Each filter has an axis of transmission that is perpendicular to the other so that when one filter is transparent, the other is not. A voltage may be applied to the electrodes, and in response the molecules of the layer are aligned to either block or allow the passage of light. An image is visible if light is blocked. The LCD 608 may be communicatively coupled to the control pressure sensor 604 to receive a signal from the control pressure sensor 604. In the some embodiments, the LCD 608 may signal operating states and other information, such as a current pressure, a pressure differential, a leak condition, a blockage condition, an overpressure condition, or a canister full condition, for example. In some embodiments, the LCD 608 may present this information in the form of text or Arabic numerals, for example.

In some embodiments, the regulator 300 may include a potentiometer 612 communicatively coupled to the adjustment shaft 336 and the dial 338. In these embodiments, the potentiometer 612 may be further communicatively coupled to the printed circuit board 602 so that at least the potentiometer 612 may transmit a voltage signal to the printed circuit board 602. The potentiometer 612 may be similar to and operate as described above with respect to the potentiometer 512 of FIG. 5.

In operation, the feedback system 600 may be fluidly coupled to the regulator 300 to determine pressures in the chambers of the regulator 300 and, in response, signal an operating state of the reduced-pressure therapy system 400. In some embodiments, for example, the operating state of the reduced-pressure system 400 can include a current pressure, a pressure differential, a leak condition, a blockage condition, a canister full condition, or an overpressure condition.

In some embodiments, the control pressure sensor 604 may be fluidly coupled to the control chamber 312, and the supply pressure sensor 614 may be fluidly coupled to the supply chamber 310. The control pressure in the control chamber 312 may be fluidly communicated to the control pressure sensor 604 through the tube 610, and the supply pressure in the supply chamber 310 may be fluidly communicated to the supply pressure sensor 614 through the tube 616. A reduced pressure may be supplied to the charging chamber 308, and the regulator 300 may operate substantially as described above to provide reduced pressure therapy. The control pressure sensor 604 may determine an amount of strain caused by the control pressure applied to the control pressure sensor 604 through the tube 610. The control pressure sensor 604 may determine a value of the control pressure in response to the measured amount of strain. Similarly, the supply pressure sensor 614 may determine an amount of strain caused by the supply pressure applied to the supply pressure sensor 614 through the tube 616. The supply pressure sensor 614 may determine a value of the supply pressure in response to the measured amount of strain.

In some embodiments, as the dressing is supplied with reduced pressure, the manifold pressure may transition from an ambient pressure to the supply pressure. The changing pressure may be fluidly communicated to the control pressure sensor 604 through the control chamber 312 and the tube 610. The control pressure sensor 604 may generate a signal corresponding to the changing control pressure determined by the control pressure sensor 604. In response, the feedback system 600 may operate the LCD 608 to display a numerical value of the control pressure corresponding to the control pressure determined by the control pressure sensor 604. In some embodiments, the numerical value may change as the control pressure changes.

The feedback system 600 may provide additional information regarding the provision of reduced-pressure therapy using the LCD 608, the supply pressure sensor 614, and the control pressure sensor 604. In some embodiments, the printed circuit board 602 may include circuitry or other components configured to monitor a difference between the control pressure determined by the control pressure sensor 604 and the supply pressure determined by the supply pressure sensor 614. For example, when a dressing may be first applied to a tissue site, the regulator 300 may be used in a draw-down process. In the draw-down process, the pressure at the dressing, the manifold pressure, is reduced from an ambient pressure to the supply pressure. The feedback system 600 may monitor the control pressure sensor 604 and the supply pressure sensor 614 to determine if the draw-down process is occurring within desired parameters. In some embodiments, the feedback system 600 may determine the difference between the control pressure determined by the control pressure sensor 604 and a supply pressure determined by the supply pressure sensor 614 and display the pressure difference or pressure differential on the LCD 608. In this manner, the feedback system 600 may signal an operating state of the dressing draw-down.

In some embodiments, if the control pressure is within the therapeutic range of the therapy pressure, the feedback system 600 may continue to monitor the control pressure determined by the control pressure sensor 604 and the supply pressure determined by the supply pressure sensor 614. If the feedback system 600 determines that the control pressure determined by the control pressure sensor 604 exceeds the lower limit of the therapeutic pressure range of the therapy pressure, and the supply pressure determined by the supply pressure sensor 614 is within the therapeutic range of the therapy pressure, then the feedback system 600 can display on the LCD 608 that a leak condition has occurred. For example, the reduced-pressure therapy system 400 may be leaking between the supply port 318 and the control port 321. Similarly, if both the control pressure sensor 604 and the supply pressure sensor 614 determine that the control pressure and the supply pressure, respectively, exceed the lower limit of the therapeutic range of the therapy pressure, then the feedback system 600 can display on the LCD 608 that a leak condition has occurred. For example, the reduced pressure therapy system may be leaking between the reduced-pressure source 402 and the source port 314.

In some embodiments, if the feedback system 600 determines that the control pressure determined by the control pressure sensor 604 remains static while the supply pressure determined by the supply pressure sensor 614 changes, such as an increase or decrease in pressure, the feedback system 600 can display on the LCD 608 that a blockage condition has occurred. For example, the supply pressure sensor 614 may determine that the supply pressure exceeds the upper limit of the therapeutic range of the therapy pressure. If the control pressure sensor 604 determines that the control pressure remains within the therapeutic range of the therapy pressure, the feedback system 600 can display on the LCD 608 that the operating state of the reduced-pressure therapy system 400 is a blockage condition.

In some embodiments, the feedback system 600 may determine if a canister full condition has occurred. For example, if the supply pressure sensor 614 determines that the supply pressure experiences a rise of reduced pressure during a preset time that exceeds a preset tolerance, and the control pressure sensor 604 determines that the control pressure in the control chamber 312 remains static, the feedback system 600 can display on the LCD 608 that a canister full condition has occurred.

The printed circuit board 602 may further include circuitry or devices configured to track the level of pressure delivered over a period of time. By tracking a level of pressure over a period of time, the feedback system 600 may determine how a pressure in a particular chamber, such as the control pressure in the control chamber 312, for example, is changing during the application of reduced-pressure therapy. In some embodiments, the feedback system 600 may further include circuitry, devices, or software to display that the pressures are changing over time on the LCD 608.

The feedback system 600 may also determine a pressure differential between a manifold pressure at a dressing and a pressure supplied to the regulator 300 to provide an indication of the efficiency of the system. For example, the feedback system 600 may determine the supply pressure in the supply chamber 310 with the supply pressure sensor 614. The feedback system 600 may also determine the control pressure in the control chamber 312 with the control pressure sensor 604. The feedback system 600 may then determine the difference between the determined pressures and display the pressure differential on the LCD 608.

The feedback system 600 may further determine when an overpressure condition has occurred. For example, the feedback system 600 may determine the supply pressure in the supply chamber 310 with the supply pressure sensor 614. The feedback system 600 may also determine the control pressure in the control chamber 312 with the control pressure sensor 604. If the supply pressure determined by the supply pressure sensor 614 and the control pressure determined by the control pressure sensor 604 exceed the upper limit of the therapeutic range of the therapy pressure, the feedback system 600 may indicate that an overpressure condition has occurred. An overpressure condition may be caused in part by a malfunction of the regulator 300 permitting excess reduced pressure to be supplied to the dressing.

In some embodiments, the therapy pressure may be selected during the manufacturing of the feedback system 600. For example, the therapy pressure may be hardwired to the printed circuit board 602. In other embodiments, the printed circuit board 602 may include a controller or central processing unit having the therapy pressure programmed into the controller or central processing unit. In other embodiments, the feedback system 600 may include an input device, such as a switch, a dial, or a keyboard, for example, that may permit an operator to input the therapy pressure. In still other embodiments, the feedback system 600 may receive a signal from the potentiometer 612 that the feedback system 600 may use to determine the therapy pressure.

In other embodiments, the feedback system 600 may be used with the regulator 200. For example, the control pressure sensor 604 may be fluidly coupled to the control chamber 206 of the regulator 200. In some embodiments, the control pressure sensor 604 may be fluidly coupled to the tee-fitting 215. The tee-fitting 215 may provide fluid communication between the control pressure sensor 604 and the control chamber 206. The supply pressure sensor 614 may be fluidly coupled to the supply chamber 204 of the regulator 200. In some embodiments, the supply pressure sensor 614 may be fluidly coupled to the tee-fitting 217. The tee-fitting 217 may provide fluid communication between the supply pressure sensor 614 and the supply chamber 204. The feedback system 600 may operate with the regulator 200 as described above with respect to the regulator 300.

In some embodiments, the regulator 200 may include monitor ports similar to the monitor ports 319 and the monitor port 323 of the regulator 300. Similarly, the regulator 300 may include tee-fittings similar to the tee-fitting 215 and the tee-fitting 217 of the regulator 200. The monitor ports and the tee-fittings may be similarly coupled to the respective regulators and operate in a similar way.

In some embodiments, the pressures measured by the feedback system 500 and the feedback system 600 may be monitored during a static time period or a revolving time period. A static time period may refer to a time period where the pressure is monitored during a an isolated period of time. For example, the feedback system 500 or the feedback system 600 may monitor a measured pressure for thirty seconds. At the conclusion of the time period, monitoring stops. A revolving time period may refer to a time period where the pressure is monitored during a continuing period of time. For example, the feedback system 500 or the feedback system 600 may monitor a measured pressure for thirty seconds. At the conclusion of the time period, monitoring restarts. In some embodiments, monitoring may compare the measured pressures across time periods.

In some embodiments, the feedback system 500 and the feedback system 600 may include wireless communication technologies, such as radio frequency identification (RFID) to provide operators with a method of retrieving therapy data such as therapy duration, pressures, and alarm conditions. In some embodiments, a secondary regulator may be positioned in-line between a reduced-pressure source and the regulator 300 to purge blockages. A secondary regulator may include a release mechanism allowing the secondary regulator to flood the charging chamber 308 with a higher pressure in an attempt to eliminate blockages. Feedback can be provided to an operator that a blockage is cleared as described above. Additionally, the system may have a relief valve to ensure that once a blockage is cleared pressure at a tissue site may not rise above a predetermined safe limit.

The feedback system 500 and the feedback system 600 may be low cost and tailored for specific regions and markets. For example, by using a single pressure sensor and an LED indicator, as illustrated with respect to FIG. 5, the cost may be substantially reduced. If additional functionality is desired, additional components, such as additional LEDs or pressure sensors may be added to provide additional information. In some forms, the feedback systems may provide a generic visual feedback as to whether reduced-pressure therapy is being effectively administered using a wall-suction source. The system may be disposable, single patient use, or reusable. By creating different functional configurations, the feedback systems can be modified to fit many needs.

The devices and systems described herein may provide variable negative pressure settings to an operator, feedback to an operator on leak conditions, feedback to an operator on blockage conditions, feedback to an operator on canister full conditions, may be low cost, may be disposable, may be for single patient use or reusable, and may be highly configurable.

It should be apparent from the foregoing that systems, methods, and apparatuses having significant advantages has been described. While shown in only a few forms, the systems, methods, and apparatuses illustrated are susceptible to various changes, modifications, and uses encompassed within the claims that follow.

We claim:
1. A reduced-pressure system comprising:
  a regulator comprising:
    a supply chamber adapted to be fluidly coupled to a dressing, a control chamber adapted to be fluidly coupled to the dressing, a charging chamber fluidly coupled to the supply chamber through a port, and a regulator valve coupled to the control chamber and operable to reciprocate at least partially within the control chamber to control fluid communication through the port based on a differential between a control pressure in the control chamber and a therapy pressure; and a feedback system comprising:

a pressure sensor adapted to be fluidly coupled to the control chamber, and a signal interface communicatively coupled to the pressure sensor and adapted to signal an operating state of the reduced-pressure system based on a pressure measured by the pressure sensor.

2. The reduced-pressure system of claim 1, wherein the pressure sensor is a first pressure sensor and the feedback system further comprises a second pressure sensor adapted to be fluidly coupled to the supply chamber to determine a supply pressure in the supply chamber.

3. The reduced-pressure system of claim 1, wherein the signal interface is a light emitting diode.

4. The reduced-pressure system of claim 1, wherein the signal interface is a liquid crystal display screen.

5. The reduced-pressure system of claim 1, wherein the regulator further comprises a potentiometer communicatively coupled to the regulator valve.

6. The reduced-pressure system of claim 1, further comprising a reduced-pressure source fluidly coupled to the charging chamber.

7. The reduced-pressure system of claim 6, further comprising a wall-suction source fluidly coupled to the charging chamber.

8. The reduced-pressure system of claim 1, further comprising the dressing adapted to be fluidly coupled to a tissue site.

9. The reduced-pressure system of claim 1, wherein the regulator valve comprises:

a valve member configured to variably engage the port; and a regulator spring coupled to the valve member and variably compressible to select the therapy pressure.

* * * * *